US012735398B2

(12) United States Patent
Guo et al.

(10) Patent No.: US 12,735,398 B2
(45) Date of Patent: Sep. 15, 2026

(54) BENZOAZEPINE COMPOUND, AND COMPOSITION AND USE THEREOF

(71) Applicants: XUZHOU MEDICAL UNIVERSITY, Jiangsu (CN); SHANGHAITECH UNIVERSITY, Shanghai (CN)

(72) Inventors: Dong Guo, Jiangsu (CN); Xudong Cao, Jiangsu (CN); Wenzhong Yan, Shanghai (CN); Jianjun Cheng, Shanghai (CN); Ying Sun, Jiangsu (CN); Limin Su, Jiangsu (CN); Ying Ren, Jiangsu (CN); Ruoqi Wang, Jiangsu (CN); Haoran Zhang, Jiangsu (CN); Haoxing Yuan, Jiangsu (CN)

(73) Assignees: XUZHOU MEDICAL UNIVERSITY, Jiangsu (CN); SHANGHAITECH UNIVERSITY, Shanghai (CN)

( * ) Notice: Subject to any disclaimer, the term of this patent is extended or adjusted under 35 U.S.C. 154(b) by 466 days.

(21) Appl. No.: 18/271,523

(22) PCT Filed: Dec. 17, 2021

(86) PCT No.: PCT/CN2021/139112

§ 371 (c)(1),
(2) Date: Jul. 10, 2023

(87) PCT Pub. No.: WO2022/156449

PCT Pub. Date: Jul. 28, 2022

(65) Prior Publication Data

US 2024/0076279 A1 Mar. 7, 2024

(30) Foreign Application Priority Data

Jan. 19, 2021 (CN) ......................... 202110067206.6

(51) Int. Cl.
*C07D 223/16* (2006.01)
*A61P 13/12* (2006.01)
*C07D 401/12* (2006.01)

(52) U.S. Cl.
CPC ............ *C07D 401/12* (2013.01); *A61P 13/12* (2018.01); *C07D 223/16* (2013.01)

(58) Field of Classification Search
CPC .................................................... C07D 223/16
See application file for complete search history.

(56) References Cited

U.S. PATENT DOCUMENTS

| | | | |
|---|---|---|---|
| 5,258,510 | A | 11/1993 | Ogawa et al. |
| 5,753,644 | A | 5/1998 | Ogawa et al. |
| 2013/0131045 | A1 | 5/2013 | Kan et al. |

FOREIGN PATENT DOCUMENTS

| | | |
|---|---|---|
| CN | 1051038 | 5/1991 |
| CN | 1091288 | 8/1994 |
| CN | 1098716 | 2/1995 |
| CN | 1107146 | 8/1995 |
| CN | 101687805 | 3/2010 |
| CN | 102753530 | 10/2012 |
| CN | 102796077 | 11/2012 |
| EP | 0 620 003 | 10/1994 |
| EP | 2 170 831 | 2/2012 |
| EP | 2 495 236 | 9/2012 |
| JP | 4-321669 | 11/1992 |
| WO | 91/05549 | 5/1991 |
| WO | 94/01113 | 1/1994 |

OTHER PUBLICATIONS

International Search Report issued Mar. 22, 2022 in International (PCT) Application No. PCT/CN2021/139112.
Matsubara et al., "An Efficient Synthesis of Optical Isomers of Vasopressin $V_2$ Receptor Antagonist OPC-41061 by Lipase-Catalyzed Enantioselective Transesterification", Heterocycles, vol. 54, No. 1, 2001, pp. 131-138.
Ohtani et al., "Efficient Synthesis of Functionalized Benzazepine Derivatives Utilizing Intramolecular Mitsunobu Reaction", Heterocycles, vol. 66, 2005.
*Registry* [Online], 2022_0021_Structure, Dec. 5, 2011.

*Primary Examiner* — Brian E McDowell
(74) *Attorney, Agent, or Firm* — Wenderoth, Lind & Ponack, L.L.P.

(57) ABSTRACT

A novel benzoazepine compound, comprising a pharmaceutically acceptable salt thereof. A pharmaceutical composition comprising the compound and a pharmaceutically acceptable salt thereof. The use of the compound and the composition in the prevention or treatment of diseases related to arginine vasopressin Vla receptor, arginine vasopressin $V_{1b}$ receptor, arginine vasopressin $V_2$ receptor, sympathetic nervous system or renin-angiotensin-aldosterone system. A method for preventing and/or treating arginine vasopressin-related diseases. The compound is represented by formula (I), wherein the substituents are defined herein:

(I)

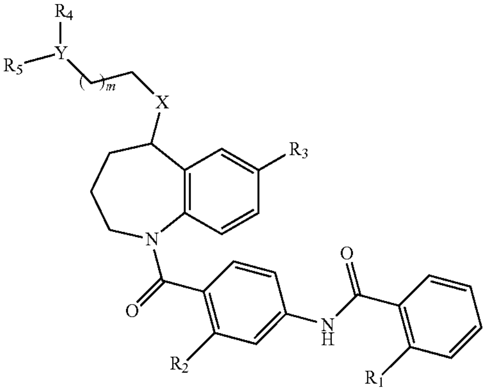

14 Claims, No Drawings

BENZOAZEPINE COMPOUND, AND COMPOSITION AND USE THEREOF

TECHNICAL FIELD

The present application relates to a novel benzoazepine compound, composition and use thereof.

BACKGROUND ART

Arginine vasopressin (AVP) is a naturally occurring neurohormone, and is released in the brain and blood. AVP plays an important role in regulating water content, blood pressure and the secretion of adrenocorticotropic hormone (ACTH), and exerts its effect on physiology and behavior by binding to specific G protein-coupled receptors in the central nervous system and certain peripheral sites or tissues. In the brain, AVP regulates circadian rhythms, promotes learning and memory in the hippocampus, and plays an important role in regulating social behavior in neurobehavioral disorders through its role in limbic circuits.

Three different AVP receptor subtypes have been identified on the basis of pharmacology and functionalism: $V_{1a}$, $V_{1b}$ and $V_2$. These receptors are located in the liver, blood vessels (coronary artery, renal vessel, and cerebral vessel), platelets, kidney, uterus, adrenal gland, pancreas, central nervous system or pituitary gland. AVP is involved in the regulation of various functions, such as functions of cardiovascular, liver, pancreas and antidiuresis and aggregation effects of platelet, as well as its roles on the central and peripheral nervous system and uterine bulb. The effect produced by the AVP receptor depends on its location. $V_{1a}$ receptors are distributed throughout the cerebral limbic system and cortex, and are distributed in vascular smooth muscle, uterus, and myocardium. $V_{1b}$ family receptors are also distributed in the limbic system and pituitary gland. The $V_2$ receptor is located in the collecting duct of the nephron in the kidney, and has become a target for the treatment of cardiovascular disease. Inhibition of arginine vasopressin receptors can produce a series of physiological effects.

Studies have shown that arginine vasopressin receptor antagonists play a positive role in the prevention and treatment of hypertension, Reye's syndrome, dysmenorrhea, premature birth, adrenocorticotropic hormone secretion disorder, adrenal hyperplasia, depression, chronic congestive heart failure, and liver cirrhosis, antidiuretic hormone secretion disorder syndrome or chronic heart failure, liver cirrhosis, hyponatremia due to antidiuretic hormone secretion disorder, and autosomal dominant polycystic kidney disease. The development of benzoazepine compounds, such as conivaptan and tolvaptan, has become a hot spot in the research and development of drugs for treating the above-mentioned diseases. Such compounds have antagonistic activity against arginine vasopressin receptors and are thus useful in the treatment of the above-mentioned diseases.

Autosomal dominant polycystic kidney disease (ADPKD) is a common inherited kidney disease with a prevalence from 1/2500 to 1/1000. ADPKD may be onset in the embryonic period, and is characterized in that fluid-filled renal cysts are the formed in the renal tubules and collecting ducts and constantly proliferate and expand, thereby damaging the normal renal parenchyma. This renal insufficiency caused by cysts will persist for decades and eventually lead to end-stage renal disease (ESRD). In addition, ADPKD may also induce a series of complications, such as hypertension, acute/chronic pain, hematuria, cyst infection and kidney stones, etc., thereby bringing great pain to patients' daily life. Therefore, exploring the pathogenesis of ADPKD and finding effective means to inhibit the progression of ADPKD has become a hot research topic.

Since ADPKD is a genetic defect disease and the selection of its drug targets is very difficult, the currently available and effective therapeutic drugs for ADPKD on the market are very scarce, and related research is still in its infancy. Based on the pathogenesis of ADPKD, the current research on its drug targets generally focuses on pathways that can regulate cell proliferation and fluid secretion, such as aquaporin-2 (AQP2), $V_2$ receptor (vasopressin-2 receptor, $V_2R$), somatostatin receptor (SSTR), ErbB-2, integrin-linked kinase (ILK), etc. Inhibition of AQP2 can significantly inhibit the expansion of vesicles caused by fluid secretion, however, it cannot significantly inhibit cell proliferation induced by ADPKD and may lead to cystic tumor lesions. SSTR acts on the G signaling pathway, and somatostatin analogs such as octreotide can activate this receptor and inhibit the formation of vesicles; however, the application of such drugs will lead to the disorder of hormone secretion in the body and have serious side effects, causing difficulties for clinical application.—Signaling pathways mediated by ErbB-2 and ILK can regulate cell proliferation, thus ErbB-2 and ILK are potential targets, and their therapeutic effects on ADPKD still need to be verified. Ganoderma triterpenes, quercetin and other Chinese herbal extracts also have a certain therapeutic effect on ADPKD, but the specific mechanism of action and adverse reactions need further research.

In terms of drug clinical research, the only effective treatment drug for ADPKD certified by the FDA (US Food and Drug Administration) is tolvaptan (OPC41061). Tolvaptan is a selective $V_2R$ antagonist, which can delay the increase in kidney volume (a surrogate marker of disease progression), slow the decline in kidney function, and relieve pain in ADPKD patients. 30 ADPKD patients are analyzed by a prospective study, and it was found that the excretion rate of sodium and urea was increased after administration of tolvaptan ($V_2R$ antagonist), indicating that $V_2R$ antagonists play an important role in maintaining the balance of water and sodium in ADPKD patients. In addition, tolvaptan can also slow down the development of ADPKD into end-stage renal disease by inhibiting the increase in kidney volume and renal damage, which means that $V_2R$ antagonists have a relieving effect on the progression of ADPKD. However, in clinical trials, while tolvaptan slowed down the decline of renal function in patients, the serum hepatic transaminases in some patients increased to more than three times the normal level, indicating that administration of tolvaptan could cause liver damage. Therefore, the FAD recommended that liver function tests should be performed on patients monthly during administration of tolvaptan, and the administration should be discontinued immediately if abnormality occurs.

In summary, although $V_2R$ antagonists can alleviate the progression of ADPKD by inhibiting cAMP (cyclic adenosine monophosphate), the clinically available drugs for ADPKD are still very scarce. Therefore, it is necessary to modify the structure of existing compounds such as tovaptan based on the structure-activity relationship of $V_2R$ antagonist compounds, thereby developing drugs with better therapeutic effects and less toxic and side effects to alleviate the occurrence of ADPKD.

As therapeutic drugs for the above diseases, benzoazepine compounds still have certain deficiencies in terms of activity, side effects, and physicochemical properties. The present application provides novel benzoazepine compounds, which have longer residence time in receptor, thereby reducing their side effects; and the benzoazepine compounds have a better inhibitory effect on the development of vesicles in PKD diseases than Tolvaptan, thereby having better effect in the treatment and prevention of such diseases.

SUMMARY

The present application relates to a novel benzoazepine compound as an arginine vasopressin receptor antagonist, and the compound in the present application has the general structure of formula (I). The present application provides a compound of formula (I) or a pharmaceutically acceptable salt thereof, (I)

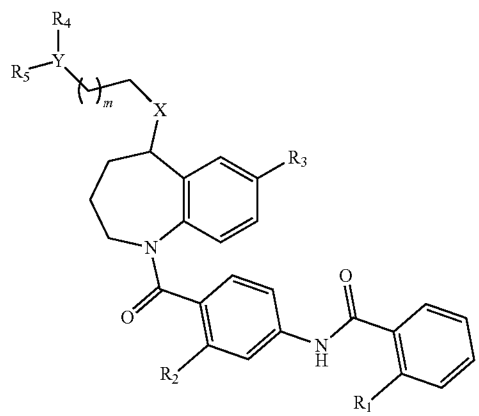

wherein

X is selected from NH, O or S;

Y is selected from N, CH, O or S;

$R_1$, $R_2$ and $R_3$ are each independently selected from hydrogen, halogen, cyano, nitro, hydroxy, amino, $C_{1-6}$ alkyl, $C_{1-6}$ alkoxy, or $C_{3-8}$ cycloalkyl;

$R_4$ and $R_5$ are each independently selected from hydrogen, halogen, cyano, nitro, hydroxy, amino, $C_{1-6}$alkyl, $C_{1-6}$alkoxy, $C_{3-8}$cycloalkyl, aryl, heteroaryl, heterocyclyl, heterocyclyl-$(CH_2)$n-, aryl-$C_{1-6}$alkyl-, heteroaryl-$C_{1-6}$alkyl-, aryl-$(CH_2)$n-O—, heteroaryl-$(CH_2)$ n-O—, $C_{3-8}$cycloalkyl-C(O)—, heterocyclyl-C(O)—, aryl-C (O)—, or heteroaryl-C(O), wherein each of $C_{1-6}$alkyl, $C_{1-6}$alkoxy, $C_{3-8}$cycloalkyl, aryl, heteroaryl, heterocyclyl, heterocyclyl-$(CH_2)$n-, aryl-$C_{1-6}$alkyl-, heteroaryl-$C_{1-6}$alkyl-, aryl-$(CH_2)$n-O—, heteroaryl-$(CH_2)$n-O—, $C_{3-8}$cycloalkyl-C(O)—, heterocyclyl-C(O)—, aryl-C (O)—, or heteroaryl-C(O) is unsubstituted or substituted with at least one substituent selected from halogen, $C_{1-6}$alkyl, $C_{1-6}$cycloalkyl, or heterocyclyl;

m is 0, 1, 2, 3 or 4;

n is 0, 1, 2, 3 or 4;

preferably, $R_1$ and $R_2$ are each independently selected from $C_{1-6}$alkyl, and $R_3$ is halogen;

preferably, both $R_1$ and $R_2$ are methyl, and $R_3$ is chlorine.

In some embodiments, in formula (I), X is NH; preferably, Y is selected from N or CH.

In some embodiments, in formula (I), $R_4$ is hydrogen or $C_{1-6}$ alkyl, and $R_5$ is selected from $C_{1-6}$ alkyl, heteroaryl, heterocyclyl, heterocyclyl-$(CH_2)$n-, heteroaryl-$C_{1-6}$ alkyl-, aryl-$(CH_2)$n-O—, or heterocyclyl-C(O)—, wherein heterocyclyl or heterocyclyl-$(CH_2)$n- is substituted by $C_{1-6}$ alkyl.

Preferably, $R_4$ is hydrogen, and $R_5$ is selected from 5-6 membered heterocyclyl, 5-6 membered heteroaryl, 5-6 membered heteroaryl-$C_{1-6}$ alkyl-, 5-10 membered aryl-$(CH_2)$n-O—, or 5-6 membered heterocyclyl-C(O)—, wherein 5-6 membered heterocyclyl or 5-6 membered heterocyclyl-$(CH_2)$n- is substituted by $C_{1-3}$ alkyl.

Preferably, $R_4$ is hydrogen, and $R_5$ is selected from 6-membered heterocyclyl, 6-membered heteroaryl, 6-membered heteroaryl-$C_{1-6}$ alkyl-, phenyl-$(CH_2)$n-O—, or 6-membered heterocyclyl —C(O)—, wherein 6-membered heterocyclyl is substituted by $C_{1-3}$ alkyl, wherein n is 0.

In some embodiments, in formula (I), $R_4$ is hydrogen, and $R_5$ is selected from 6-membered heterocyclyl, 6-membered heterocyclyl-C(O)—, or 6-membered heterocyclyl substituted by methyl.

Preferably, the heterocyclyl comprises one or two N or O heteroatoms as ring atoms;

Preferably, $R_4$ is hydrogen, $R_5$ is

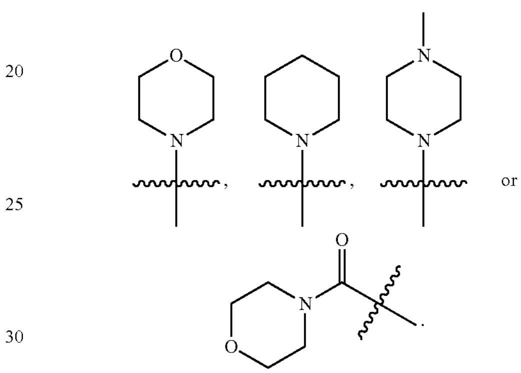

In some embodiments, in formula (I), $R_4$ is hydrogen, and $R_5$ is selected from 6-membered heteroaryl, 6-membered heteroaryl-$C_{1-6}$ alkyl-, or benzene-$(CH_2)$n-O—.

Preferably, the heteroaryl comprises an N or O heteroatom as a ring atom.

Preferably, $R_4$ is hydrogen, and $R_5$ is

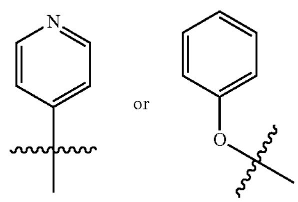

In some embodiments, in formula (I), $R_4$ is $C_{1-6}$ alkyl, and $R_5$ is $C_{1-6}$ alkyl; preferably, $R_4$ is $C_{1-3}$ alkyl, and $R_5$ is $C_{1-3}$ alkyl; preferably, both $R_4$ and $R_5$ are ethyl.

The present application further provides some preferred technical solutions about the compound represented by formula (I), and the compound is:

1) N-(4-(7-chloro-5-((3-morpholinopropyl)amino)-2,3,4,5-tetrahydro-1H-benzo[b]azepine-1-carbonyl)-3-methylphenyl)-2-methylbenzamide;

2) N-(4-(7-chloro-5-((4-morpholinobutyl)amino)-2,3,4,5-tetrahydro-1H-benzo[b]azepine-1-carbonyl)-3-methylphenyl)-2-methylbenzamide;

3) N-(4-(7-chloro-5-((5-morpholinopentyl)amino)-2,3,4,5-tetrahydro-1H-benzo[b]azepine-1-carbonyl)-3-methylphenyl)-2-methylbenzamide;

4) N-(4-(7-chloro-5-((2-morpholinoethyl)amino)-2,3,4,5-tetrahydro-1H-benzo[b]azepine-1-carbonyl)-3-methylphenyl)-2-methylbenzamide;

5)N-(4-(7-chloro-5-((3-(pyridin-4-yl)propyl)amino)-2,3,4,5-tetrahydro-1H-benzo[b]azepine-1-carbonyl)-3-methylphenyl)-2-methylbenzamide;

6)N-(4-(7-chloro-5-((2-(pyridin-4-yl)ethyl)amino)-2,3,4,5-tetrahydro-1H-benzo[b]azepine-1-carbonyl)-3-methylphenyl)-2-methylbenzamide;

7)N-(4-(7-chloro-5-((4-(pyridin-4-yl)butyl)amino)-2,3,4,5-tetrahydro-1H-benzo[b]azepine-1-carbonyl)-3-methylphenyl)-2-methylbenzamide;

8)N-(4-(7-chloro-5-((5-(pyridin-4-yl)pentyl)amino)-2,3,4,5-tetrahydro-1H-benzo[b]azepine-1-carbonyl)-3-methylphenyl)-2-methylbenzamide;

9)N-(4-(7-chloro-5-((3-(piperidin-1-yl)propyl)amino)-2,3,4,5-tetrahydro-1H-benzo [b]azepine-1-carbonyl)-3-methylphenyl)-2-methylbenzamide;

10)N-(4-(7-chloro-5-((2-(piperidin-1-yl)ethyl)amino)-2,3,4,5-tetrahydro-1H-benzo[b]azepine-1-carbonyl)-3-methylphenyl)-2-methylbenzamide;

11)N-(4-(7-chloro-5-((4-(piperidin-1-yl)butyl)amino)-2,3,4,5-tetrahydro-1H-benzo[b]azepine-1-carbonyl)-3-methylphenyl)-2-methylbenzamide;

12)N-(4-(7-chloro-5-((5-(piperidin-1-yl)pentyl)amino)-2,3,4,5-tetrahydro-1H-benzo[b]azepine-1-carbonyl)-3-methylphenyl)-2-methylbenzamide;

13)N-(4-(7-chloro-5-((3-morpholino-3-oxopropyl)amino)-2,3,4,5-tetrahydro-1H-benzo[b]azepine-1-carbonyl)-3-methylphenyl)-2-methylbenzamide;

14)N-(4-(7-chloro-5-((4-morpholino-4-oxobutyl)amino)-2,3,4,5-tetrahydro-1H-benzo[b]azepine-1-carbonyl)-3-methylphenyl)-2-methylbenzamide;

15)N-(4-(7-chloro-5-((5-morpholino-5-oxopentyl)amino)-2,3,4,5-tetrahydro-1H-benzo[b] azepine-1-carbonyl)-3-methylphenyl)-2-methylbenzamide;

16)N-(4-(7-chloro-5-((6-morpholino-6-oxohexyl)amino)-2,3,4,5-tetrahydro-1H-benzo[b]azepine-1-carbonyl)-3-methylphenyl)-2-methylbenzamide;

17)N-(4-(7-chloro-5-((3-(4-methylpiperazin-1-yl)propyl)amino)-2,3,4,5-tetrahydro-1H-benzo[b] azepine-1-carbonyl)-3-methylphenyl)-2-methylbenzamide;

18)N-(4-(7-chloro-5-((2-(4-methylpiperazin-1-yl)ethyl)amino)-2,3,4,5-tetrahydro-1H-benzo[b] azepine-1-carbonyl)-3-methylphenyl)-2-methylbenzamide;

19)N-(4-(7-chloro-5-((4-(4-methylpiperazin-1-yl)butyl)amino)-2,3,4,5-tetrahydro-1H-benzo[b] azepine-1-carbonyl)-3-methylphenyl)-2-methylbenzamide;

20)N-(4-(7-chloro-5-((5-(4-methylpiperazin-1-yl)pentyl)amino)-2,3,4,5-tetrahydro-1H-benzo[b]azepine-1-carbonyl)-3-methylphenyl)-2-methylbenzamide;

21)N-(4-(7-chloro-5-((2-phenoxyethyl)amino)-2,3,4,5-tetrahydro-1H-benzo[b] azepine-1-carbonyl)-3-methylphenyl)-2-methylbenzamide;

22)N-(4-(7-chloro-5-((3-phenoxypropyl)amino)-2,3,4,5-tetrahydro-1H-b enzo [b]azepine-1-carbonyl)-3-methylphenyl)-2-methylbenzamide;

23)N-(4-(7-chloro-5-((4-phenoxybutyl)amino)-2,3,4,5-tetrahydro-1H-benzo[b]azepine-1-carbonyl)-3-methylphenyl)-2-methylbenzamide;

24)N-(4-(7-chloro-5-((5-phenoxypentyl)amino)-2,3,4,5-tetrahydro-1H-benzo[b]azepine-1-carbonyl)-3-methylphenyl)-2-methylbenzamide;

25)N-(4-(7-chloro-5-((3-(diethylamino)propyl)amino)-2,3,4,5-tetrahydro-1H-benzo[b]azepine-1-carbonyl)-3-methylphenyl)-2-methylbenzamide;

26)N-(4-(7-chloro-5-((2-(diethylamino)ethyl)amino)-2,3,4,5-tetrahydro-1H-benzo[b]azepine-1-carbonyl)-3-methylphenyl)-2-methylbenzamide;

27)N-(4-(7-chloro-5-((4-(diethylamino)butyl)amino)-2,3,4,5-tetrahydro-1H-benzo[b]azepine-1-carbonyl)-3-methylphenyl)-2-methylbenzamide; or 28)N-(4-(7-chloro-5-((5-(diethylamino)pentyl)amino)-2,3,4,5-tetrahydro-1H-benzo[b]azepine-1-carbonyl)-3-methylphenyl)-2-methylbenzamide.

In some embodiments, the pharmaceutically acceptable salt is a salt formed by reacting the compound of formula (I) with an inorganic or organic acid; preferably, the inorganic acid is hydrochloric acid, hydrobromic acid, sulfuric acid or phosphoric acid, and the organic acid is citric acid, lactic acid, malic acid, gluconic acid, tartaric acid, adipic acid, acetic acid, succinic acid, fumaric acid, ascorbic acid, itaconic acid, methanesulfonic acid or benzenesulfonic acid.

In another aspect, the present application also provides a pharmaceutical composition comprising a therapeutically effective dose of a compound of formula (I) or a pharmaceutically acceptable salt thereof, and one or more pharmaceutically acceptable carriers.

The present application further provides use of the compound of the present application, or a pharmaceutically acceptable salt thereof, or the above-mentioned pharmaceutical composition in the preparation of a medicament;

preferably, the medicament is used for the prevention or treatment of diseases related to arginine vasopressin $V_{1a}$ receptor, arginine vasopressin $V_{1b}$ receptor, arginine vasopressin $V_2$ receptor, sympathetic nervous system or renin-angiotensin-aldosterone system;

preferably, the diseases related to arginine vasopressin $V_{1a}$ receptor, arginine vasopressin $V_{1b}$ receptor, arginine vasopressin $V_2$ receptor, sympathetic nervous system or renin-angiotensin-aldosterone system comprise: hypertension, Reye's syndrome, dysmenorrhea, premature birth, corticotropin-releasing hormone secretion disorder, adrenal hyperplasia, depression, chronic congestive heart failure, liver cirrhosis, antidiuretic hormone secretion disorder syndrome, hyponatremia due to chronic heart failure/liver cirrhosis/antidiuretic hormone secretion disorder, or polycystic kidney disease.

The present application further provides a method for preventing and/or treating arginine vasopressin-related diseases, and the method comprises administering to a subject the compound of the present application or a pharmaceutically acceptable salt thereof or the above-mentioned pharmaceutical composition.

Preferably, the compound or a pharmaceutically acceptable salt thereof or the above-mentioned pharmaceutical composition is provided in a therapeutically effective amount.

In one embodiment, the subject is a mammal.

In one embodiment, the mammal includes a human, a non-human primate, a rabbit, a sheep, a rat, a dog, a cat, a pig, or a mouse. The non-human primate includes, but is not limited to: a monkey, a chimpanzee, a gorilla, an ape, a lemur, a macaque, and a gibbon. In a preferred embodiment, the non-human primate is a monkey or a chimpanzee. In some cases, the subject is a human.

In some embodiments, the arginine vasopressin-related disease comprises the diseases related to arginine vasopressin $V_{1a}$ receptor, arginine vasopressin $V_{1b}$ receptor, arginine vasopressin $V_2$ receptor, sympathetic nervous system or renin-angiotensin-aldosterone system.

Preferably, the diseases comprise hypertension, Reye's syndrome, dysmenorrhea, premature birth, corticotropin-releasing hormone secretion disorder, adrenal hyperplasia, depression, chronic congestive heart failure, liver cirrhosis, antidiuretic hormone secretion disorder syndrome, hyponatremia due to chronic heart failure/liver cirrhosis/antidiuretic hormone secretion disorder, or polycystic kidney disease.

The present application also provides a method for inhibiting the effect of arginine vasopressin in a subject in need thereof, and the method comprises administering to the subject the compound of the present application or a pharmaceutically acceptable salt thereof or the mentioned pharmaceutical composition, to reduce the effect of arginine vasopressin in a subject.

In one embodiment, the subject is a mammal.

In one embodiment, the mammal includes a human, a non-human primate, a rabbit, a sheep, a rat, a dog, a cat, a pig, or a mouse. The non-human primate includes, but is not limited to: a monkey, a chimpanzee, a gorilla, an ape, a lemur, macaque, and a gibbon. In a preferred embodiment, the non-human primate is a monkey or a chimpanzee. In some cases, the subject is a human.

Unless otherwise stated, the chemical terms used in the above general structural formulas have the usual meaning.

For example, "halogen" used in the present application refers to fluorine, chlorine, bromine or iodine, unless otherwise specified. Preferably, "halogen" is fluorine, chlorine or bromine.

In the present application, unless otherwise specified, "alkyl" refers to a linear or branched monovalent saturated hydrocarbon group with at most 10 carbon atoms. Representative examples of alkyl groups include, but are not limited to: methyl, ethyl, n-propyl, isopropyl, n-butyl, isobutyl, sec-butyl, tert-butyl, n-pentyl, 3-(2-methyl)butyl, 2-pentyl, 2-methylbutyl, neopentyl, n-hexyl, 2-hexyl, 2-methylpentyl, 3-methylhexyl, 2,2-dimethylpentyl, 2,3-dimethylpentyl, n-heptyl, n-octyl, n-nonyl, n-decyl, etc. Similarly, "$C_{1-6}$" in "$C_{1-6}$ alkyl" refers to groups with 1, 2, 3, 4, 5 or 6 carbon atoms in a straight or branched arrangement. Substituted alkyl groups are alkyl groups comprising one or more substituents in place of hydrogens, for example, 1, 2 or 3 substituents, and at most the number of substituents is that of the hydrogens present on the unsubstituted alkyl group. Unless otherwise stated, suitable substituents for alkyl may be selected from halogen, CN, oxo, hydroxy, $C_{1-4}$ alkoxy, substituted or unsubstituted $C_{3-6}$ cycloalkyl, substituted or unsubstituted phenyl, amino, ($C_{1-4}$ alkyl)amino, di($C_{1-4}$ alkyl)amino, $C_{1-4}$ alkylthio, $C_{1-4}$ alkylsulfonyl, —C(═O)—$C_{1-4}$ alkyl, COOH, COO($C_{1-4}$ alkyl), —O(C═O)—$C_{1-4}$ alkyl, —NHC(═O)$C_{1-4}$ alkyl and —NHC(═O)O$C_{1-4}$ alkyl; wherein, for substituted cycloalkyl or phenyl, the substituents are at most three groups selected from the group consisting of: Me, Et, —OMe, —OEt, CF3, halogen, CN, OH and $NH_2$.

In the present application, unless otherwise stated, the term "alkoxy" refers to alkyl-O—, wherein alkyl is as defined above. Representative examples of alkoxy include, but are not limited to: methoxy, ethoxy, propoxy, 2-propoxy, butoxy, tert-butoxy, pentyloxy, hexyloxy, and the like. Usually, the alkoxy group has 1-6, more usually 1-4 carbon atoms.

In the present application, unless otherwise stated, the term "cycloalkyl" refers to a saturated or unsaturated non-aromatic monocyclic, bicyclic, tricyclic or spirocyclic hydrocarbon group with 3-12 carbon atoms. The cycloalkyl group may be unsaturated, and may be fused to another ring which may be saturated, unsaturated or aromatic, provided that the ring atom of the cycloalkyl group to which the target formula is attached is not an aromatic ring carbon. Unless otherwise specified, cycloalkyl refers to a cyclic hydrocarbon group with 3 to 9 ring carbon atoms or 3 to 7 ring carbon atoms. Preferably, unless otherwise specified, cycloalkyl refers to a saturated monocyclic group with 3-7 ring atoms, for example, cyclopropyl, cyclobutyl, cyclopentyl and cyclohexyl.

In the present application, unless otherwise specified, the term "heterocyclyl" refers to a heterocyclic group that is saturated or partially unsaturated but not aromatic, and may be monocyclic or polycyclic (in the case of being polycyclic, especially being bicyclic, tricyclic or spiro); and has 3 to 14, more commonly 4 to 10, most preferably 5 or 6 ring atoms; in which one or more, preferably one to four, especially one or two ring atoms are heteroatoms each independently selected from O, S, and N (the remaining ring atoms are carbon atoms). Even if described as, for example, a $C_{5-6}$ atomic ring, a heterocyclic ring contains at least one heteroatom as a ring atom with the other ring atoms being carbon atoms, and the ring has said number of ring atoms, for example 5-6 in this example. Preferably, a heterocyclyl has one or two such heteroatoms as ring atoms, and preferably, the heteroatoms are not directly connected to each other. Unless otherwise stated, a bonded ring (i.e., a ring connected to the target formula) preferably has 4-12, especially 5-7 ring atoms. A heterocyclic group may be fused to an aromatic ring, provided that the atom of the heterocyclic group attached to the target formula is not aromatic. The heterocyclic group may be attached to the target formula through a heteroatom (usually nitrogen) or a carbon atom on the heterocyclic group. The heterocyclic group may comprise fused or bridged rings as well as spiro rings, as long as one ring of the polycyclic heterocyclic group contains a heteroatom as a ring atom. The heterocyclyl group may be attached to any heteroatom or carbon atom to form a stable structure. Examples of such heterocyclyl groups include, but are not limited to: tetrahydrofuranyl (THF), dihydrofuranyl, 1,4-dioxanyl, morpholinyl, 1,4-dithioxanyl, piperazinyl, piperidinyl, 1,3-dioxolanyl, imidazolidinyl, imidazolinyl, pyrrolinyl, pyrrolidinyl, tetrahydropyranyl, dihydropyranyl, oxathiolanyl, dithiolanyl, 1,3-dioxanyl, 1,3-dithioxanyl, oxathianyl, thiomorpholinyl and the like.

Similarly, each heterocyclyl moiety of other groups such as "heterocyclyloxy", "heterocyclyloxyalkyl", "heterocyclyloxycarbonyl" shall have the same meaning as in the above definition of "heterocyclyl".

In the present application, unless otherwise specified, the term "aryl" refers to an aromatic hydrocarbon group having 6-14 carbon atoms in the ring moiety. Typically, aryl groups are monocyclic, bicyclic or tricyclic aryl groups having 6-14 carbon atoms, usually 6-10 carbon atoms, for example, phenyl or naphthyl. Additionally, the term "aryl" as used herein refers to an aromatic substituent, which may be a single aromatic ring, or multiple aromatic rings fused together. Non-limiting examples include: phenyl, naphthyl, and 1,2,3,4-tetrahydronaphthyl, provided that the tetrahydronaphthyl group is attached to the target molecular formula through a carbon of the aromatic ring of the tetrahydronaphthyl group. Unless otherwise stated, the preferred aryl group is phenyl.

In the present application, unless otherwise stated, the term "heteroaryl" refers to a 5-14 membered monocyclic or bicyclic or tricyclic aromatic ring system with 1 to 8 heteroatoms as ring atoms and the remaining rings atoms being carbon, and the heteroatoms are selected from N, O and S. Typically, heteroaryl groups are 5-10 membered ring systems, especially 5-6 membered monocyclic or 8-10 membered bicyclic groups. Heteroaryl groups may be attached to any heteroatom or carbon atom to form a stable structure. Examples of heteroaryl groups include, but are not limited to: thienyl, furyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzoisoxazolyl, benzothiazolyl, benzothiazolyl, benzothiadiazolyl, benzotriazolyl adenine, quinolyl or isoquinolyl.

The terms "substituted" or "substitute" refer to the substitution of one or more hydrogen atoms in a group with the same or a different substituent, respectively. Typical substituents include but are not limited to: halogen (F, Cl, Br or I), $C_{1-8}$ alkyl, $C_{3-12}$ cycloalkyl, $—OR_1$, $—SR_1$, $=O$, $=S$, $—C(O)R_1$, $—C(S)R_1$, $=NR_1$, $—C(O)OR_1$, $—C(S)OR_1$, $—NR_1R_1$, $—C(O)NR_1R_1$, cyano, nitro, $—S(O)_2R_1$, $—O—S(O_2)\ OR_1$, $—O—S(O)_2R_1$, $—OP(O)(OR_1)(OR_2)$; wherein $R_1$ and $R_2$ are each independently selected from —H, $C_{1-6}$ alkyl, or $C_{1-6}$ haloalkyl. In some embodiments, the substituents are independently selected from the group consisting of: —F, —Cl, —Br, —I, —OH, trifluoromethoxy, ethoxy, propoxy, isopropoxy, n-butoxy, isobutoxy, tert-butoxy, $—SCH_3$, $—SC_2H_5$, formyl, $—C(OCH_3)$, cyano, nitro, $—CF_3$, $—OCF_3$, amino, dimethylamino, methylthio, sulfonyl and acetyl.

The compounds of the present application are capable of forming acid and/or base salts due to the presence of amino and/or carboxyl or similar groups. As used herein, the term "salt" or "salts" refers to an acid addition salt or base addition salt of the compound of the present application. "Salt" specifically includes "pharmaceutically acceptable salt". The term "pharmaceutically acceptable salt" refers to a salt that retains the biological effectiveness and properties of the compounds of the present application, and generally meets the requirements biologically or otherwise; especially, a salt prepared from a pharmaceutically acceptable non-toxic base or acid. When the compounds provided herein are acids, their corresponding salts can be conveniently prepared from pharmaceutically acceptable non-toxic bases, including inorganic and organic bases. Salts derived from inorganic bases include aluminum, ammonium, calcium, copper (high valent and low valent), ferric iron, ferrous iron, lithium, magnesium, manganese (high valent and low valent), potassium, sodium, zinc, and the like. The salts of ammonium, calcium, magnesium, potassium and sodium are particularly preferred. Pharmaceutically acceptable nontoxic organic bases that can be derivatized into salts include primary, secondary, and tertiary amines, as well as cyclamines and substituted amines, such as naturally occurring and synthetic substituted amines. Other pharmaceutically acceptable nontoxic organic bases capable of forming salts, include ion exchange resins and arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, reduced glucosamine, glucosamine, histidine, hydrabamine, isopropylamine, lysine, methylglucosamine, morpholine, piperazine, piperidine, polyamine resin, procaine, purine, theobromine, triethylamine, trimethylamine, tripropylamine, tromethamine, etc.

When the compounds provided by the present application are bases, their corresponding salts can be conveniently prepared from pharmaceutically acceptable non-toxic acids, including inorganic and organic acids. Such acids include inorganic and organic acids, for example, acetic acid, benzenesulfonic acid, benzoic acid, camphorsulfonic acid, citric acid, ethanesulfonic acid, formic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid and p-toluenesulfonic acid, etc. Preferably, the inorganic acid is hydrochloric acid, hydrobromic acid, sulfuric acid or phosphoric acid, etc., and the organic acid is citric acid, lactic acid, malic acid, gluconic acid, tartaric acid, adipic acid, acetic acid, succinic acid, fumaric acid, antiseptic acid, itaconic acid, methanesulfonic acid or benzenesulfonic acid, etc. Since the compound represented by formula (I) will be used as a medicament, it is preferable to use a certain purity, for example, at least 60% pure, more suitably at least 75% pure, particularly suitably at least 98% pure (% is weight ratio).

The pharmaceutically acceptable salts of the present application may be synthesized from basic or acidic moieties by conventional chemical methods. Generally, these salts can be prepared by reacting the free acid forms of these compounds with a stoichiometric amount of an appropriate base (e.g., Na, Ca, Mg, or K, hydroxide, carbonate, bicarbonate, etc.), or by reacting the free base forms of these compounds with a stoichiometric amount of an appropriate acid. Such reactions are usually carried out in water or in organic solvents, or in a mixture of both. Generally, where feasible, it is desirable to use a non-aqueous medium such as ether, ethyl acetate, tetrahydrofuran, toluene, chloroform, dichloromethane, methanol, ethanol, isopropanol or acetonitrile.

Prodrugs of the compounds of the present application are included within the protection scope of the present application. In general, the prodrugs refer to functional derivatives that are readily converted into the desired compound in vivo. For example, any pharmaceutically acceptable salt, ester, salt of ester or other derivative of the compound of the present application, upon administration to a recipient, is capable of directly or indirectly providing the compound of the present application or its pharmaceutically active metabolite or residue. Particularly preferred derivatives or prodrugs are those that can increase the bioavailability of the compounds of the present application when administered to a patient (e.g., make orally administered compounds more readily absorbed into the blood), or those that promote the delivery of the parent compound to biological organs or the action sites (e.g., the brain or lymphatic system). Therefore, the term "administration" in the treatment methods provided by the present application refers to the administration of the compounds disclosed in the present application that can treat different diseases, or the compounds which (although not explicitly disclosed) can be transformed into the compounds disclosed in the present application in vivo after administration to a subject. Conventional methods for the selection and preparation of suitable prodrug derivatives are described, for example, in books such as Design of Prodrugs (Design of Prodrugs, ed. H. Bundgaard, Elsevier, 1985).

The compounds of the present application may contain one or more asymmetric centers, and may thereby give rise to diastereomers and optical isomers. The present application comprises all possible diastereomers and racemic mixtures thereof, substantially pure resolved enantiomers thereof, all possible geometric isomers and pharmaceutically acceptable salts thereof.

The above-mentioned formula (I) does not exactly define the steric structure of the compound at a certain position. The present application comprises all stereoisomers of the compounds represented by formula (I) and pharmaceutically acceptable salts thereof. Further, mixtures of stereoisomers and isolated specific stereoisomers are also included in the present application. During the process of preparing such compounds, or during the process of using racemization or epimerization well known to those skilled in the art, the resulting product may be a mixture of stereoisomers. When the compound represented by formula (I) has a tautomer, unless otherwise stated, the present application comprises any possible tautomer and a pharmaceutically acceptable salt thereof, and a mixture thereof.

When the compound represented by formula (I) and a pharmaceutically acceptable salt thereof have a solvate or a polymorph, the present application includes any possible solvate and polymorph. The type of solvent used for forming a solvate is not particularly limited as long as the solvent is pharmaceutically acceptable. For example, water, ethanol, propanol, acetone and similar solvents may be used.

Therefore, the pharmaceutical composition of the present application comprises a pharmaceutically acceptable carrier and a compound represented by formula (I) or its stereoisomer, tautomer, polymorph, solvate, a pharmaceutically acceptable salt thereof, a prodrug thereof. The compound represented by formula (I) or a pharmaceutically acceptable salt thereof, and one or more other compounds with therapeutic activity which will be administrated in combination with it are also comprised in the pharmaceutical composition of the present application.

In the present application, the term "composition" refers to a product comprising a specified amount of each specified ingredient, as well as any product produced directly or indirectly from a combination of the specified amount of each specified ingredient. Accordingly, the pharmaceutical composition comprising the compound of the present application as the active ingredient and the method for preparing the compound of the present application are also part of the present application. In addition, some of the crystalline forms of the compound may exist as polymorphs, and such polymorphs are included in the present application. In addition, some compounds may form solvates with water (i.e., hydrates) or common organic solvents, and such solvates also fall within the scope of the present application.

The pharmaceutical composition provided by the present application comprises the compound represented by formula (I) (or a pharmaceutically acceptable salt thereof) as an active component, a pharmaceutically acceptable excipient, and other optional therapeutic components or adjuvants. Although the most suitable administration mode of the active component in any given situation will depend on the particular subject to be administered with the active component, the characters of the subject and the severity of the condition, the pharmaceutical composition of the present application comprises those suitable for oral, rectal, topical and parenteral (including subcutaneous, intramuscular, intravenous) administration. The pharmaceutical composition of the present application may conveniently be presented in unit dosage form well known in the art, and prepared by any preparation method well known in the art of pharmacy.

In fact, based on conventional pharmaceutical admixing techniques, the compound represented by formula (I) of the present application, or a prodrug, or a metabolite, or a pharmaceutically acceptable salt thereof can be used as an active component to mix with a pharmaceutical carrier to form a pharmaceutical composition. The pharmaceutical carrier can take a wide variety of forms depending on the desired administration mode, e.g., oral or injection administration (including intravenous injection). Accordingly, the pharmaceutical compositions of the present application may be presented in discrete units suitable for oral administration, such as capsules, cachets or tablets containing a predetermined dose of the active component. Further, the pharmaceutical compositions of the present application may take the form of powders, granules, solutions, aqueous suspensions, non-aqueous liquids, oil-in-water emulsions, or water-in-oil emulsions. Moreover, in addition to the common dosage forms mentioned above, the compound represented by formula (I) or a pharmaceutically acceptable salt thereof can also be administered by a controlled release manner and/or a delivery device. The pharmaceutical composition of the present application can be prepared by any pharmaceutical method. In general, such methods comprise the step of associating the active ingredient with the carrier which constitutes one or more essential ingredients. In general, the pharmaceutical compositions are prepared by uniform intimate admixture of the active ingredient with a liquid carrier or a finely divided solid carrier, or a mixture of both. In addition, the product can be easily prepared into the desired appearance.

In the present application, the term "pharmaceutically acceptable carrier" includes any and all solvents, dispersion media, coatings, surfactants, antioxidants, preservatives (e.g., antibacterial, antifungal), isotonic agents, absorption retardants, salts, preservatives, pharmaceutical stabilizers, binders, excipients, disintegrants, lubricants, sweeteners, flavors, dyes, etc., and combinations thereof, as known by those skilled in the art (see, e.g., Remington: The Science and Practice of Pharmacy, 22nd Edition). In addition to any conventional carrier incompatible with the active ingredient, its use in therapeutic or pharmaceutical compositions is also contemplated. The term "therapeutically effective amount" of the compound of the present application refers to an amount of the compound of the present application that elicits a biological or medical response in a subject, e.g., an amount sufficient to reduce one or more symptoms, alleviate a condition, slow or delay disease progression, or prevent disease, etc. In one non-limiting embodiment, the term "therapeutically effective amount" refers to such an amount of the compound of the present application, when administered to a subject it is effective to prevent or treat diseases related to arginine vasopressin $V_{1a}$ receptor, arginine vasopressin $V_{1b}$ receptor, arginine vasopressin $V_2$ receptor, sympathetic nervous system or renin-angiotensin-aldosterone system.

As used herein, the term "subject" refers to any organism to which the composition of the present application may be administered, e.g., for experimental, diagnostic and/or therapeutic purposes. Typical subjects include animals (e.g., mammals, such as non-human primates and humans; birds; domestic or farm animals, such as cats, dogs, sheep, goats, cattle, horses, and pigs; laboratory animals, such as mice, rats and guinea pigs; rabbits; fish; reptiles).

In particular, the pharmaceutical carrier used in the present application may be, for example, a solid carrier, a liquid carrier or a gaseous carrier. Solid carriers include, but are not limited to: lactose, gypsum powder, sucrose, talc, gelatin, agar, pectin, acacia, magnesium stearate and stearic acid. Liquid carriers include, but are not limited to: syrup, peanut oil, olive oil and water. Gaseous carriers include, but not limited to: carbon dioxide and nitrogen. In preparing a pharmaceutical oral formulation, any pharmaceutically convenient medium may be used. For example, water, glycols, oils, alcohols, flavor enhancers, preservatives, colorants, etc. may be used in oral liquid formulations such as suspensions, elixirs and solutions; and carriers such as starches, saccharides, microcrystalline cellulose, diluents, granulating agents, lubricants, binders, disintegrants, etc. may be used for oral solid formulations such as powders, capsules and tablets. For ease of administration, tablets and capsules are preferred for oral formulations, where solid pharmaceutical carriers are used. Alternatively, standard aqueous or non-aqueous formulation techniques may be used for coating tablets.

Tablets containing the compound or pharmaceutical composition of the present application may be formed by compression or molding, optionally the tablets may be prepared by the compound or pharmaceutical composition together with one or more accessory components or adjuvant. Compressed tablets may be prepared by compressing in a suitable machine a mixture of the active ingredient in a free-flowing form (such as powder or granules) and a binder, lubricant, inert diluent, surfactant, or dispersant. Molded tablets may be prepared by wetting the powdered compound or pharmaceutical composition with an inert liquid diluent and then molding in a suitable machine. Tablets may be film coating or enteric coating according to methods known in the art. Preferably, each tablet contains about 0.05 mg to 5 g of active ingredient, and each cachet or capsule contains about 0.05 mg to 5 g of active ingredient. For example, a formulation intended for oral administration in humans contains about 0.5 mg to about 5 g of the active ingredient in combination with suitable and conveniently metered auxiliary materials, wherein the auxiliary materials account for 5% to 95% of the total amount of the pharmaceutical composition. A unit dosage form generally contains about 1 mg to about 2 g, typically 25 mg, 50 mg, 100 mg, 200 mg, 300 mg, 400 mg, 500 mg, 600 mg, 800 mg, or 1000 mg of the active ingredient.

The pharmaceutical compositions of the present application may be certain injectable compositions which are aqueous isotonic solutions or suspensions, and suppositories are advantageously prepared from fatty emulsions or suspensions. The compositions may be sterile and/or contain adjuvants such as preservatives, stabilizers, wetting or emulsifying agents, solution promoters, salts for adjusting the osmotic pressure and/or buffers. In addition, they may also contain other substances with therapeutic value. The compositions are prepared according to conventional methods for mixing, granulating or coating respectively, and contain about 0.1-75% or about 1-50% of the active ingredient.

The pharmaceutical compositions of the present application may be suitable compositions for transdermal administration, and comprise an effective amount of a compound of the present application and a suitable carrier. Carriers suitable for transdermal delivery include absorbable, pharmacologically acceptable solvents to facilitate passing through the skin of the host. For example, a transdermal device is in the form of a bandage, and comprises a backing member, a reservoir containing the compound and optionally a carrier, optionally a rate-controlling barrier for delivering the compound to the skin of the host at a controlled and predetermined rate over a long period of time, and a means of securing the device to the skin.

The pharmaceutical compositions of the present application may be suitable compositions for topical administration (e.g., to the skin and eyes), and comprise aqueous solutions, suspensions, ointments, creams, gels, or sprayable formulations, e.g., for delivery by aerosol, etc. These topical delivery systems may involve, for example, inhalation or intranasal application suitable for the treatment of influenza, and may contain solubilizers, stabilizers, tension enhancers, buffers and preservatives. With or without a suitable propellant, they can be conveniently delivered from a dry powder inhaler in the form of a dry powder (individually, as a mixture, for example with lactose, or mixed component particles, for example with phospholipids), or are delivered to pressurized containers, pumps, sprayers, atomizer, or nebulizers in the form of an aerosol spray.

For a human subject of about 50-70 kg, a unit dose of the pharmaceutical composition or a combination of the present application may contain about 1-1000 mg of active ingredient(s), or about 1-500 mg, or about 1-250 mg, or about 1-150 mg, or about 0.5-100 mg, or about 1-50 mg of active ingredient. The therapeutically effective dose of the compound, pharmaceutical composition or combination thereof depends on the species, weight, age and individual condition of the subject, the disorder or disease being treated or its severity. A physician, clinician or veterinarian of ordinary skill can readily determine the effective amount of each active ingredient necessary to prevent, treat or inhibit the progression of a condition or disease.

In general, to treat the conditions or discomforts indicated above, the dosage level of the drug is about 0.01 mg/kg body weight to 150 mg/kg body weight per day, or 0.5 mg to 7 g per patient per day. For example, for inflammation, cancer, psoriasis, allergy/asthma, diseases and discomforts in the immune system, diseases and discomforts in the central nervous system (CNS), the dosage level of the drug for the effective treatment is 0.01 mg/kg body weight to 50 mg/kg body weight per day, or 0.5 mg to 3.5 g per patient per day. However, it will be appreciated that lower or higher doses than those described above may be required. The specific dosage level and treatment regimen for any particular patient will depend on a variety of factors, including the activity of the specific compound to be used, age, body weight, general health condition, sex, and diet of the patient, time of administration, route of administration, excretion rate, the situation of drug combination and the severity of the specific disease to be treated.

DETAILED DESCRIPTION

The following examples are intended to illustrate the application and should not be construed to limit it. Temperatures are given in degrees Celsius. If not mentioned otherwise, all evaporations are carried out under reduced pressure, usually about 15 mmHg to 100 mmHg (about 20-133 mbar). The structures of final products, intermediates and starting materials are confirmed by standard analytical methods such as microanalysis and spectroscopic characterization such as MS, IR, NMR. All parts and percentages herein are calculated by weight, and all temperatures are in degrees Celsius. The compounds described herein are commercially available, or can be synthesized by the following conventional methods from commercially available starting materials and reagents. Abbreviations used in the present application are conventional abbreviations in the art. Some abbreviations in the present application are listed as follows.

Abbreviations

MS: mass spectrometry
IR: infrared absorption spectroscopy
NMR: nuclear magnetic resonance spectroscopy
HRMS: high resolution mass spectrometry
ESI: electrospray ion source
Tolvaptan: tolvaptan
EA: ethyl acetate
$MnO_2$: manganese dioxide
DCM: dichloromethane
MeOH: methanol
$NaBH_4$: sodium borohydride
N-CBZ-beta-alanine: benzyloxycarbonyl-beta-alanine
DMF: N,N-dimethylformamide HATU: 2-(7-azabenzotriazole)-N,N,N',N'-tetramethylurea hexafluorophosphate DIPEA: N,N-diisopropylethylamine Pd: palladium $CDCl_3$: deuterated chloroform DMSO: dimethyl sulfoxide $CO_2$: carbon dioxide NaOH: sodium hydroxide; Tween: Tween PEG: polyethylene glycol μM: molarity (micromoles per liter)

nM: molarity (nanomoles per liter)

M: molarity (moles per liter)

° C.: degrees celsius h: hours min: minutes $V_2R$: vasopressin-2-receptor

AC enzyme: eukaryotic adenylate cyclase

Forskolin: adenylate cyclase activator

PKD: polycystic kidney disease

Compounds 1-28 in the specific Examples of the present application are derivatives of tolvaptan. In these compounds, X in the general formula is NH, and for the preparation method of Compounds 1-28, tovaptan is used as the starting material to be oxidized by manganese dioxide to obtain corresponding Intermediate IV, and then the Intermediate IV and the corresponding amine are reduced by enamine to obtain the target product (Compounds 1-28).

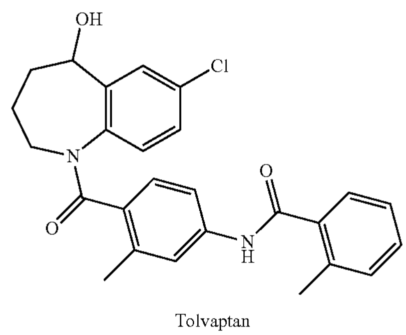

Tolvaptan

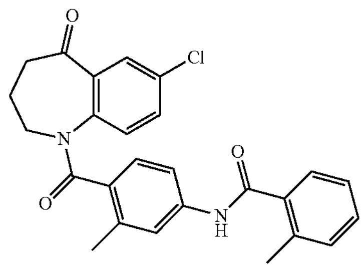

IV

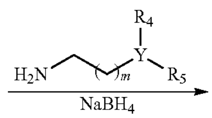

-continued

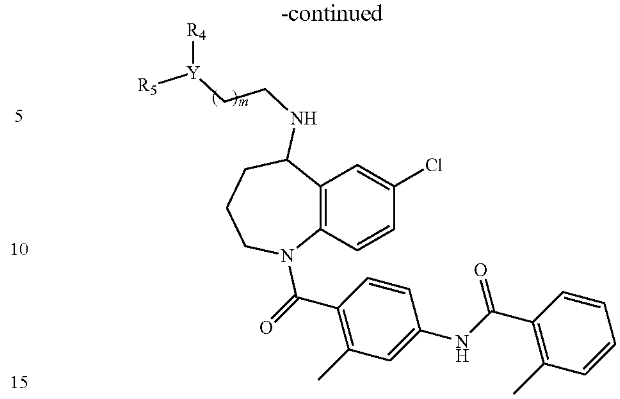

Example 1

Preparation of N-(4-(7-chloro-5-((3-morpholinopropyl)amino)-2,3,4,5-tetrahydro-1H-benzo[b]azepine-1-carbonyl)-3-methylphenyl)-2-methylbenzamide (Compound 1)

Step 1: Preparation of N-(4-(7-chloro-5-oxo-2,3,4,5-tetrahydro-1H-benzo[b]azepine-1-carbonyl)-3-methylphenyl)-2-methylbenzamide (Intermediate IV):

IV

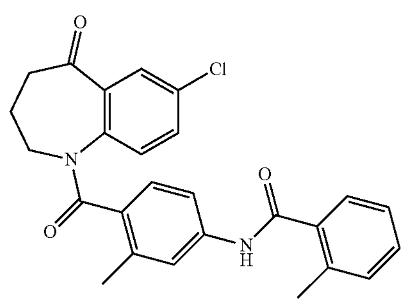

Tolvaptan (1.0 g, 2.23 mmol) was dissolved in dichloromethane (30 mL), active manganese dioxide (1.0 g) was added, and the mixture was stirred under reflux overnight. The solvent was evaporated to dryness under reduced pressure, and the solid residue was purified by silica gel column chromatography (eluent: 100% EA) to obtain Intermediate IV (0.90 g, yield: 90.4%) as a pale yellow oil.

HRMS (ESI) calculated for $C_{26}H_{24}Cl\ N_2O_3^+[M+H]^+$ 447.1470; Found:447.1473

Step 2: Preparation of N-(4-(7-chloro-5-((3-morpholinopropyl)amino)-2,3,4,5-tetrahydro-1H-benzo[b]azepine-1-carbonyl)-3-methylphenyl)-2-methylbenzamide (Compound 1):

1

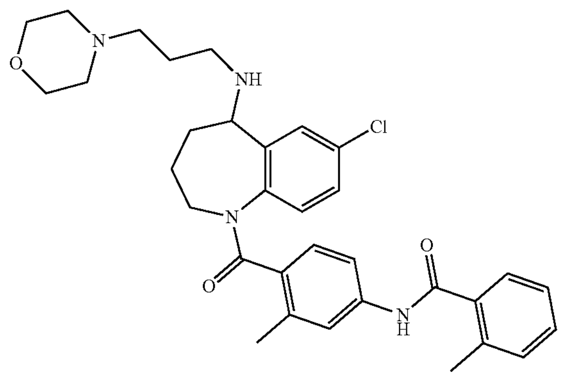

Intermediate IV (0.80 g, 1.79 mmol) and N-(3-aminopropyl)morpholine (0.52 g, 3.61 mmol) were dissolved in dry tetrahydrofuran (40 mL). Glacial acetic acid was added dropwise to adjust the pH of the reaction solution to about 6, and the reaction solution was refluxed for 2 hours under nitrogen protection. Methanol (20 mL) was added to the reaction solution, and then sodium borohydride (0.20 g, 5.29 mmol). The resulting mixture was continually stirred under reflux for 40 minutes. The solvent was evaporated to dryness under reduced pressure, and the solid residue was purified by silica gel column chromatography (eluent: MeOH/DCM=1:10) to obtain Compound 1 (0.50 g, yield: 48.6%) as a white foam.

$^1$H NMR (800 MHz, $CDCl_3$) δ7.83-6.41 (m, 10H), 4.54-3.98 (m, 1H), 3.92-3.55 (m, 5H), 3.22-2.91 (m, 1H), 2.90-2.67 (m, 2H), 2.67-2.37(m, 12H), 2.11-1.43 (m, 6H). HRMS (ESI) calculated for $C_{33}H_{40}ClN_4O_3^+[M+H]^+$575.2783; Found:575.2781.

Example 2

Preparation of N-(4-(7-chloro-5-((4-morpholinobutyl)amino)-2,3,4,5-tetrahydro-1H-benzo[b]azepine-1-carbonyl)-3-methylphenyl)-2-methylbenzamide (Compound 2)

Step 1: Preparation of 4-morpholinobutyronitrile (Intermediate V):

V

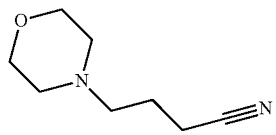

4-chlorobutyronitrile (0.90 g, 8.69 mmol) was dissolved in morpholine (4.0 mL), the mixture was stirred at room temperature overnight, and then it was separated by silica gel column chromatography (eluent: Me0H/DCM=1:20) to obtain the Intermediate V (0.85 g, yield: 63%) as a pale yellow transparent liquid. $^1$H NMR (800 MHz, $CDCl_3$) δ3.75-3.65 (m, 4H), 2.54-2.33 (m, 8H), 1.87-1.78 (m, 2H). HRMS (ESI) calculated for $C_8H_{15}N_2O^+[M+H]^+$155.1179; Found:155.1178.

Step 2: Preparation of 4-morpholino-1-butylamine (Intermediate VI):

VI

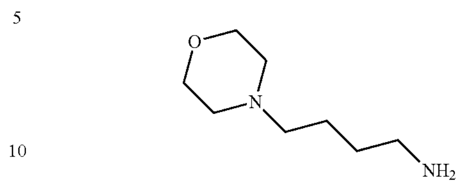

Intermediate V (0.31 g, 2 mmol) was dissolved in methanol (10 mL), and then palladium/carbon catalyst (10% Pd, 300 mg) and concentrated hydrochloric acid (0.5 mL) were added. The mixture was stirred at 45° C. for 2 hours under hydrogen atmosphere. The palladium/carbon catalyst was filtered off, and the solvent was evaporated to dryness under reduced pressure. The solid residue was dissolved in methanol, and sodium methoxide (216 mg, 4 mmol) was added to the solution. The methanol was evaporated to dryness again, and the solid residue was dissolved in dichloromethane; then the solid sodium chloride was removed by filtration, and the dichloromethane was evaporated to dryness under reduced pressure to obtain crude Intermediate VI (219 mg, directly used in the next step without further purification) as a pale yellow liquid. HRMS (ESI) calculated for $C_8H_{19}N_2O^+[M+H]^+$159.1492; Found: 159.1495.

Step 3: Preparation of N-(4-(7-chloro-5-((4-morpholinobutyl)amino)-2,3,4,5-tetrahydro-1H-benzo[b]azepine-1-carbonyl)-3-methylphenyl)-2-methylbenzamide (Compound 2):

2

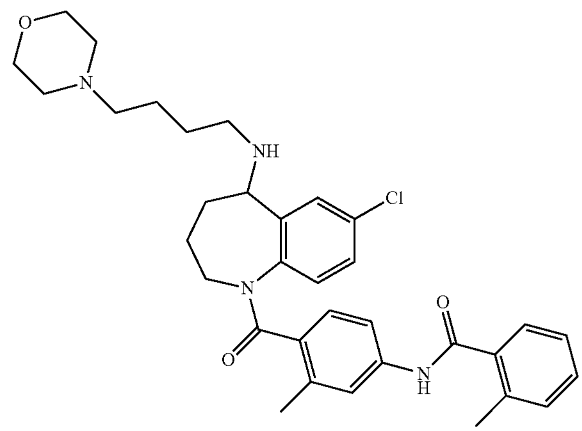

N-(3-aminopropyl)morpholine in step 2 of Example 1 was replaced with Intermediate VI, and the rest of the required raw materials, reagents and preparation methods were the same as those in step 2 of Example 1, Compound 2 was obtained as a white foam. $^1$H NMR (800 MHz, $CDCl_3$) δ7.70-6.45 (m, 10H), 4.55-3.99 (m, 1H), 3.96-3.46 (m, 5H), 3.24-3.04 (m, 1H), 2.75-2.42 (m,14H), 2.12-1.98 (m, 2H), 1.82-1.44 (m, 6H). HRM (ESI) calculated for $C_{34}H_{42}ClN_4O_3^+[M+H]^+$589.2940; Found:589.2942.

Example 3

Preparation of N-(4-(7-chloro-5-((5-morpholinopentyl)amino)-2,3,4,5-tetrahydro-1H-benzo[b]azepine-1-carbonyl)-3-methylphenyl)-2-methylbenzamide (Compound 3):

3

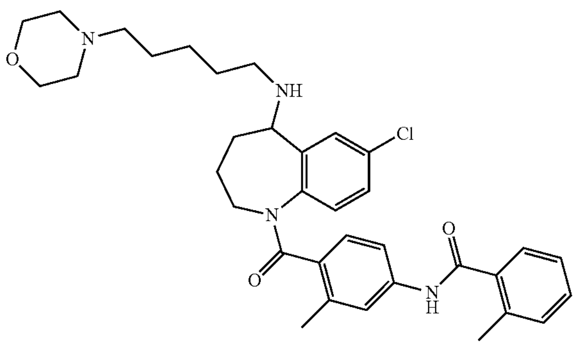

The 4-chlorobutyronitrile in step 1 of Example 2 was replaced with 5-bromovaleronitrile, and the rest of the required raw materials, reagents and preparation methods were the same as those in Example 2, Compound (I-3) was obtained as a white foam. $^1$H NMR (800 MHz, $CDCl_3$) δ 7.70-6.45 (m, 10H), 4.57-4.01 (m, 1H), 3.87-3.64 (m, 5H), 3.21—3.05 (m, 1H), 2.71-2.39 (m, 14H), 2.11-1.97 (m, 2H), 1.81-1.32 (m, 8H). HRMS (ESI) calculated for $C_{35}H_{44}ClN_4O_3^+$[M+H]$^+$603.3096; Found: 603.3098.

Example 4

Preparation of N-(4-(7-chloro-5-((2-morpholinoethyl)amino)-2,3,4,5-tetrahydro-1H-benzo[b]azepine-1-carbonyl)-3-methylphenyl)-2-methylbenzamide (Compound 4):

4

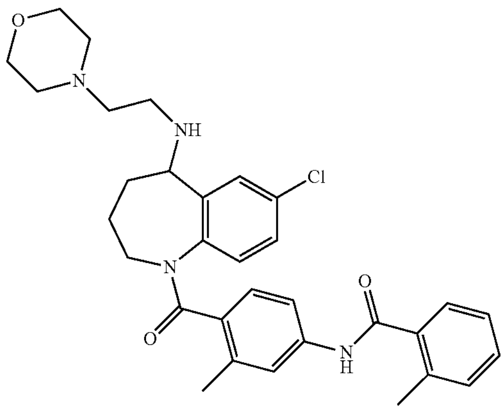

N-(3-aminopropyl)morpholine in step 2 of Example 1 was replaced with N-(2-aminoethyl)morpholine, and the rest of the required raw materials, reagents and preparation methods were the same as those in step 2 of Example 1, Compound 4 was obtained as a white foam. $^1$H NMR (800 MHz, DMSO-$d_6$) δ 10.41-10.16 (m, 1H), 7.79-6.47 (m, 10H), 4.44-3.92 (m, 1H), 3.89-3.41 (m, 5H), 3.08-2.87 (m, 1H), 2.77-2.57 (m, 2H), 2.46-2.26(m,12H), 2.06-1.61 (m, 2H), 1.55-1.27 (m,2H). HRMS (ESI) calculated for $C_{32}H_{38}ClN_4O_3^+$[M+H]$^+$561.2627; Found: 561.2624.

Example 5

Preparation of N-(4-(7-chloro-5-((3-(pyridin-4-yl)propyl)amino)-2,3,4,5-tetrahydro-1H-benzo[b]azepine-1-carbonyl)-3-methylphenyl)-2-methylbenzamide (Compound 5):

5

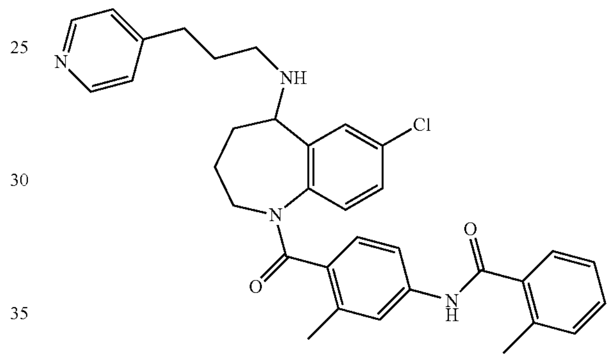

N-(3-aminopropyl)morpholine in step 2 of Example 1 was replaced with 3-(4-pyridyl) propylamine, and the rest of the required raw materials, reagents and preparation method were the same as those in step 2 of Example 1, Compound 5 was obtained as a white foam. $^1$H NMR (800 MHz, $CDCl_3$) δ 8.54-8.34 (m, 2H), 8.01 — 6.39 (m, 12H), 4.50 — 3.94 (m, 1H), 3.83-3.07 (m, 2H), 2.84-2.34 (m, 10H), 2.05-1.41 (m, 6H). HRMS (ESI) calculated for $C_{34}H_{36}ClN_4O_2^+$[M+H]$^+$567.2521; Found: 567.2518.

Compounds 6-8 shown in Table 1 were prepared by using the corresponding intermediates essentially according to the method described in Example 5.

TABLE 1

| Compound No | Chemical name | Structural formula | Physical data (MS) $(M + H)^+$ |
|---|---|---|---|
| 6 | N-(4-(7-chloro-5-((2-(pyridin-4-yl)ethyl)amino)-2,3,4,5-tetrahydro-1H-benzo[b]azepine-1-carbonyl)-3-methylphenyl)-2-methylbenzamide | 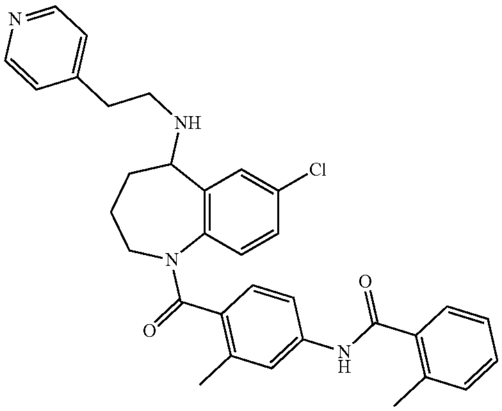 [SMILES: Cc1ccccc1C(=O)Nc1ccc(C(=O)N2CCCC(NCCc3ccncc3)c3cc(Cl)ccc32)c(C)c1] | 553.2365 |
| 7 | N-(4-(7-chloro-5-((4-(pyridin-4-yl)butyl)amino)-2,3,4,5-tetrahydro-1H-benzo[b]azepine-1-carbonyl)-3-methylphenyl)-2-methylbenzamide | 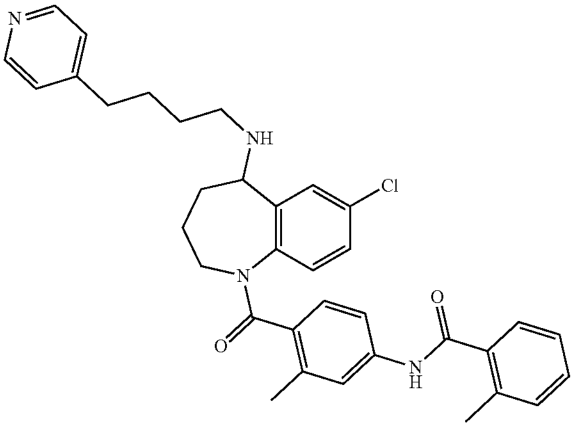 [SMILES: Cc1ccccc1C(=O)Nc1ccc(C(=O)N2CCCC(NCCCCc3ccncc3)c3cc(Cl)ccc32)c(C)c1] | 581.2678 |
| 8 | N-(4-(7-chloro-5-((5-(pyridin-4-yl)pentyl)amino)-2,3,4,5-tetrahydro-1H-benzo[b]azepine-1-carbonyl)-3-methylphenyl)-2-methylbenzamide | 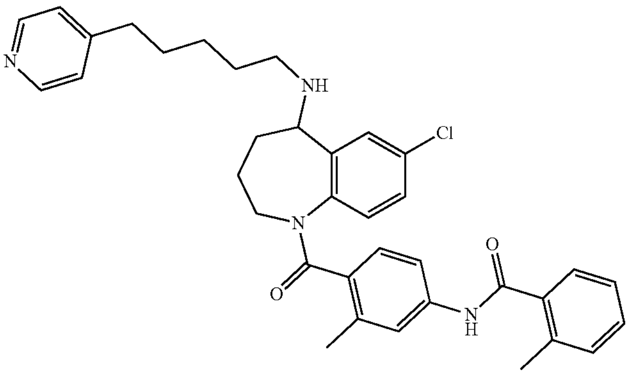 [SMILES: Cc1ccccc1C(=O)Nc1ccc(C(=O)N2CCCC(NCCCCCc3ccncc3)c3cc(Cl)ccc32)c(C)c1] | 595.2834 |

Example 6

Preparation of N-(4-(7-chloro-5-((3-(piperidin-1-yl)propyl)amino)-2,3,4,5-tetrahydro-1H-benzo[b]azepine-1-carbonyl)-3-methylphenyl)-2-methylbenzamide (Compound 9):

9

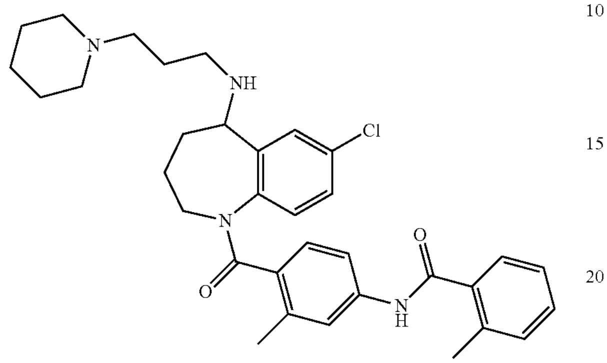

The N-(3-aminopropyl)morpholine in step 2 of Example 1 was replaced with 1-(3-aminopropyl)piperidine, and the rest of the required raw materials, reagents and preparation methods were the same as those in step 2 of Example 1, Compound 9 was obtained as a white foam. $^1$H NMR (800 MHz, $CDCl_3$) δ 7.79-6.31 (m, 10H), 4.51-3.11 (m, 3H), 2.90-2.34 (m, 14H), 2.08-1.37 (m, 12H). HRMS (ESI) calculated for $C_{34}H_{42}ClN_4O_2^+$[M+H]$^+$573.2991; Found: 573.2984.

Compounds 10-12 shown in Table 2 were prepared by using the corresponding intermediates essentially according to the method described in Example 6.

TABLE 2

| Compound No | Chemical name | Structural formula | Physical data (MS) (M + H)$^+$ |
|---|---|---|---|
| 10 | N-(4-(7-chloro-5-((2-(piperidin-1-yl)ethyl)amino)-2,3,4,5-tetrahydro-1H-benzo[b]azepine-1-carbonyl)-3-methylphenyl)-2-methylbenzamide | 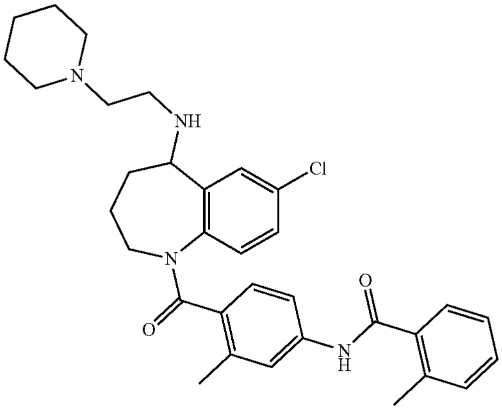 [SMILES: Cc1ccccc1C(=O)Nc1ccc(C(=O)N2CCCC(NCCN3CCCCC3)c3cc(Cl)ccc32)c(C)c1] | 559.2834 |
| 11 | N-(4-(7-chloro-5-((4-(piperidin-1-yl)butyl)amino)-2,3,4,5-tetrahydro-1H-benzo[b]azepine-1-carbonyl)-3-methylphenyl)-2-methylbenzamide | 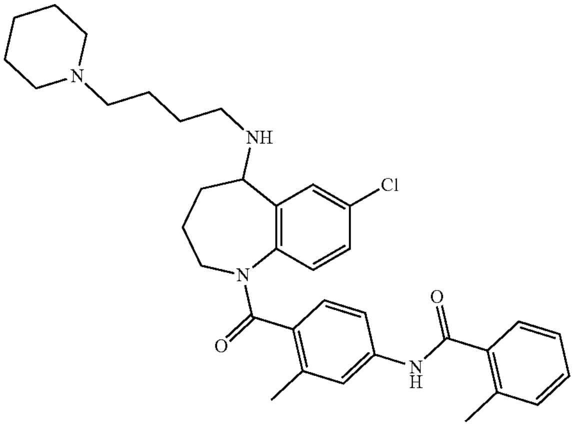 [SMILES: Cc1ccccc1C(=O)Nc1ccc(C(=O)N2CCCC(NCCCCN3CCCCC3)c3cc(Cl)ccc32)c(C)c1] | 587.3147 |

TABLE 2-continued

| Compound No | Chemical name | Structural formula | Physical data (MS) (M + H)$^+$ |
|---|---|---|---|
| 12 | N-(4-(7-chloro-5-((5-(piperidin-1-yl)pentyl)amino)-2,3,4,5-tetrahydro-1H-benzo[b]azepine-1-carbonyl)-3-methylphenyl)-2-methylbenzamide | 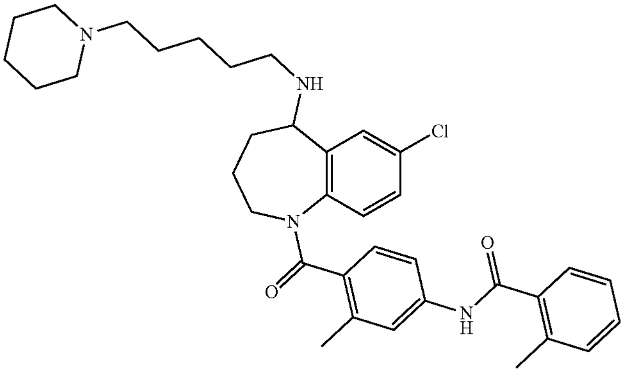 [SMILES: Cc1ccccc1C(=O)Nc1ccc(C(=O)N2CCCC(NCCCCCN3CCCCC3)c3cc(Cl)ccc32)c(C)c1] | 601.3304 |

Example 7

Preparation of N-(4-(7-chloro-5-((3-morpholino-3-oxopropyl)amino)-2,3,4,5-tetrahydro-1H-benzo[b]azepine-1-carbonyl)-3-methylphenyl)-2-methylbenzamide (Compound 13):

Step 1: Preparation of benzyl (3-morpholino-3-oxopropyl)carbamate (Intermediate VII):

VII

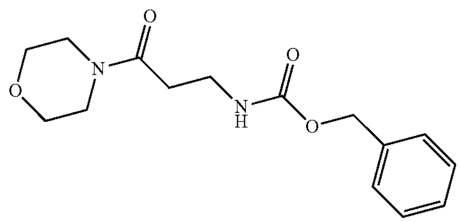

N—CBZ-beta-alanine (2.23 g, 10 mmol) was dissolved in anhydrous DMF (30 mL), then HATU (7.6 g, 20 mmol) was added, and the mixture was stirred at room temperature for 20 minutes. Then morpholine (0.87g, 10 mmol) and DIPEA (3.87 g, 30 mmol) were added, stirring at room temperature overnight. The reaction solution was diluted with water, extracting three times with ethyl acetate. The organic phases were combined, the solvent was evaporated under reduced pressure, and the remaining solid was separated and purified by silica gel column chromatography to obtain Intermediate VII (1.31 g, yield 45%). $^1H$ NMR (800 MHz, $CDCl_3$) δ 7.38-7.28 (m, 5H), 5.61 (s, 1H), 5.08 (s, 2H), 3.68-3.63 (m, 4H), 3.62-3.56 (m, 2H), 3.53-3.46 (m, 2H), 3.44-3.38 (m, 2H), 2.52 (t, J=5.6 Hz, 2H). HRMS (ESI) calculated for $C_{15}H_{21}N_2O_4^+[M+H]^+$293.1496, Found: 293.1491.

Step 2: Preparation of 3-amino-1-morpholinopropan-1-one (Intermediate VIII):

VIII

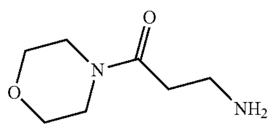

Intermediate VII (1.2 g, 4.1 mmol) was dissolved in methanol (40 mL), and palladium/carbon catalyst (10% Pd, 400 mg) was added. The mixture was stirred at room temperature under hydrogen atmosphere for 5 hours. The palladium/carbon catalyst was filtered off, and the solvent was evaporated to dryness under reduced pressure to obtain the crude Intermediate VIII (0.57 g, directly used in the next step without further purification). HRMS(ESI) calculated for $C_7H_{15}N_2O_2^+[M+H]^+$159.1128; Found: 159.1125.

Step 3: Preparation of N-(4-(7-chloro-5-((3-morpholino-3-oxopropyl)amino)-2,3,4,5-tetrahydro-1H-benzo[b]azepine-1-carbonyl)-3-methylphenyl)-2-methylbenzamide (Compound 13):

13

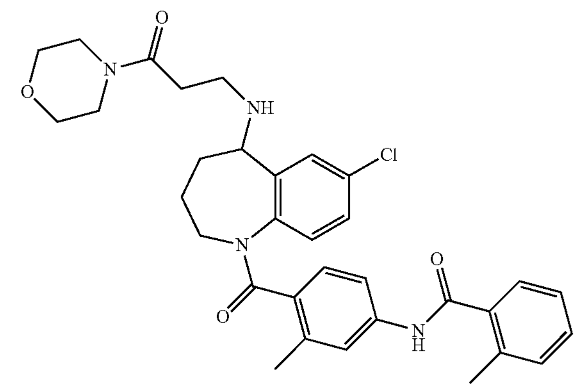

N-(3-aminopropyl)morpholine in step 2 of Example 1 was replaced with Intermediate VIII, and the rest of the required raw materials, reagents and preparation methods were the same as those in step 2 of Example 1, Compound 13 was obtained as a white foam. $^1H$ NMR (800 MHz, $CDCl_3$) δ 7.82-6.28 (m, 10H), 4.52-4.05 (m, 1H), 3.81-3.32 (m, 9H), 3.19-2.06 (m, 11H), 2.06-1.40 (m, 4H). HRMS (ESI) calculated for $C_{33}H_{38}ClN_4O_4^+[M+H]^+$589.2576; Found: 589.2571.

Compounds 14-16 shown in Table 3 were prepared by using the corresponding intermediates essentially according to the method described in Example 7.

TABLE 3

| Compound No | Chemical name | Structural formula | Physical data (MS) $(M + H)^+$ |
|---|---|---|---|
| 14 | N-(4-(7-chloro-5-((4-morpholino-4-oxobutyl)amino)-2,3,4,5-tetrahydro-1H-benzo[b]azepine-1-carbonyl)-3-methylphenyl)-2-methylbenzamid | 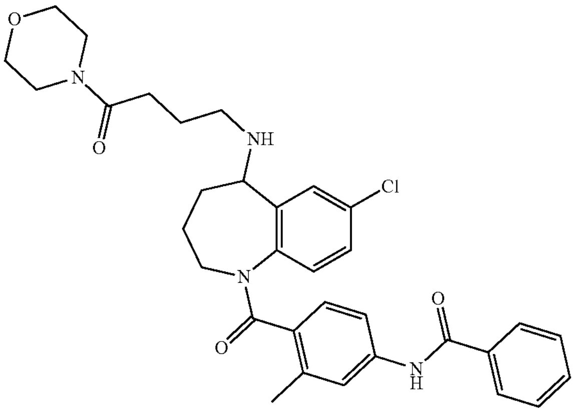 [SMILES: Cc1cc(NC(=O)c2ccccc2)ccc1C(=O)N1CCCC(NCCCC(=O)N2CCOCC2)c2cc(Cl)ccc21] | 603.2733 |
| 15 | N-(4-(7-chloro-5-((5-morpholino-5-oxopentyl)amino)-2,3,4,5-tetrahydro-1H-benzo[b]azepine-1-carbonyl)-3-methylphenyl)-2-methylbenzamide | 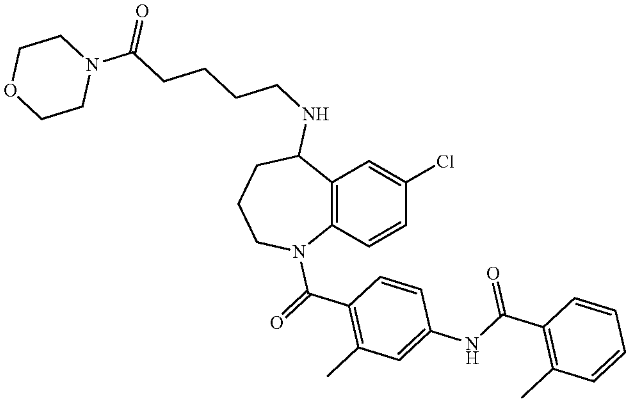 [SMILES: Cc1ccccc1C(=O)Nc1ccc(C(=O)N2CCCC(NCCCCC(=O)N3CCOCC3)c3cc(Cl)ccc32)c(C)c1] | 617.2889 |
| 16 | N-(4-(7-chloro-5-((6-morpholino-6-oxohexyl)amino)-2,3,4,5-tetrahydro-1H-benzo[b]azepine-1-carbonyl)-3-methylphenyl)-2-methylbenzamide | 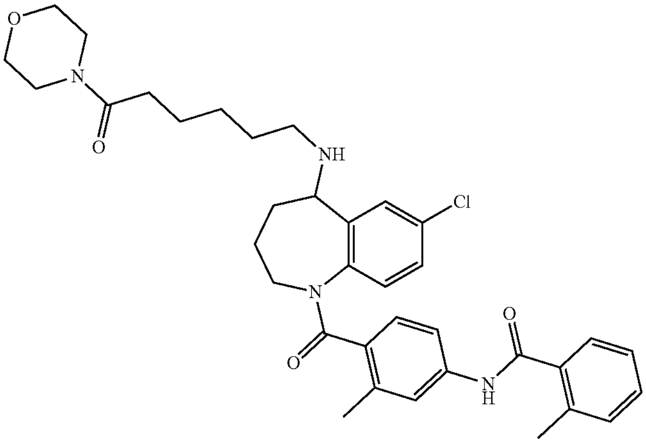 [SMILES: Cc1ccccc1C(=O)Nc1ccc(C(=O)N2CCCC(NCCCCCC(=O)N3CCOCC3)c3cc(Cl)ccc32)c(C)c1] | 631.3046 |

Example 8

Preparation of N-(4-(7-chloro-5-((3-(4-methylpiperazin-1-yl)propyl)amino)-2,3,4,5-tetrahydro-1H-benzo[b]azepine-1-carbonyl)-3-methylphenyl)-2-methylbenzamide (Compound 17):

17

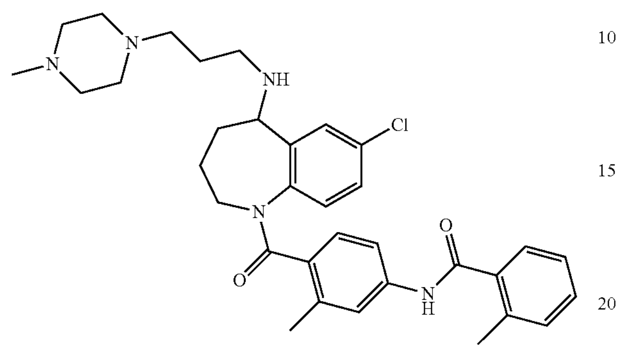

N-(3-aminopropyl)morpholine in step 2 of Example 1 was replaced with 1-(3-aminopropyl)-4-methylpiperazine, and the rest of the required raw materials, reagents and preparation method were the same as those in step 2 of Example 1, Compound (1-8) was obtained as a white foam. $^1H$ NMR(800 MHz, $CDCl_3$) δ8.02-6.41(m,10H),4.50-3.14(m,3H),2.92-2.28(m,21H),2.11-1.36(m,6H). HRMS (ESI) calculated for $C_{34}H_{43}ClN_5O_2^+$[M+H]$^+$588.3100; Found: 588.3097.

Compounds 18-20 shown in Table 4 were prepared by using the corresponding intermediates essentially according to the method described in Example 8.

TABLE 4

| Compound No | Chemical name | Structural formula | Physical data (MS) (M + H)$^+$ |
|---|---|---|---|
| 18 | N-(4-(7-chloro-5-((2-(4-methylpiperazin-1-yl)ethyl)amino)-2,3,4,5-tetrahydro-1H-benzo[b]azepine-1-carbonyl)-3-methylphenyl)-2-methylbenzamide | 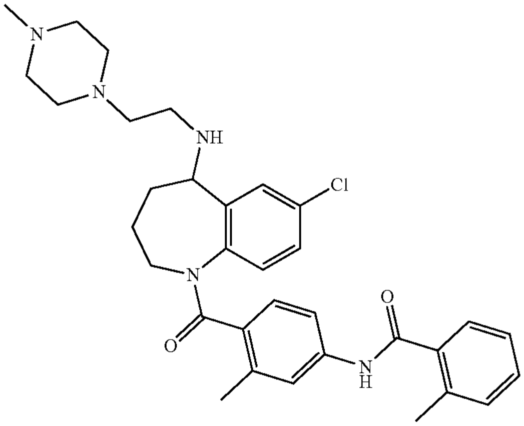 [SMILES: Cc1ccccc1C(=O)Nc1ccc(C(=O)N2CCCC(NCCN3CCN(C)CC3)c3cc(Cl)ccc32)c(C)c1] | 574.1943 |
| 19 | N-(4-(7-chloro-5-((4-(4-methylpiperazin-1-yl)butyl)amino)-2,3,4,5-tetrahydro-1H-benzo[b]azepine-1-carbonyl)-3-methylphenyl)-2-methylbenzamide | 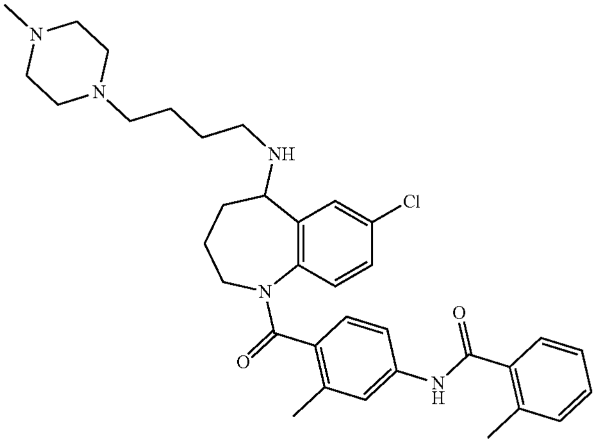 [SMILES: Cc1ccccc1C(=O)Nc1ccc(C(=O)N2CCCC(NCCCCN3CCN(C)CC3)c3cc(Cl)ccc32)c(C)c1] | 602.3256 |

TABLE 4-continued

| Compound No | Chemical name | Structural formula | Physical data (MS) (M + H)+ |
| --- | --- | --- | --- |
| 20 | N-(4-(7-chloro-5-((5-(4-methylpiperazin-1-yl)pentyl)amino)-2,3,4,5-tetrahydro-1H-benzo[b]azepine-carbonyl)-3-methylphenyl)-2-methylbenzamide | 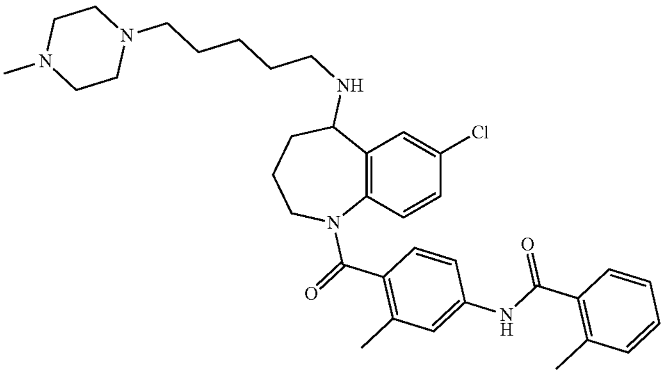 [SMILES: Cc1ccccc1C(=O)Nc1ccc(C(=O)N2CCCC(NCCCCCN3CCN(C)CC3)c3cc(Cl)ccc32)c(C)c1] | 616.3413 |

Example 9

Preparation of N-(4-(7-chloro-5-((2-phenoxyethyl)amino)-2,3,4,5-tetrahydro-1H-benzo[b]azepine-1-carbonyl)-3-methylphenyl)-2-methylbenzamide (Compound 21):

21

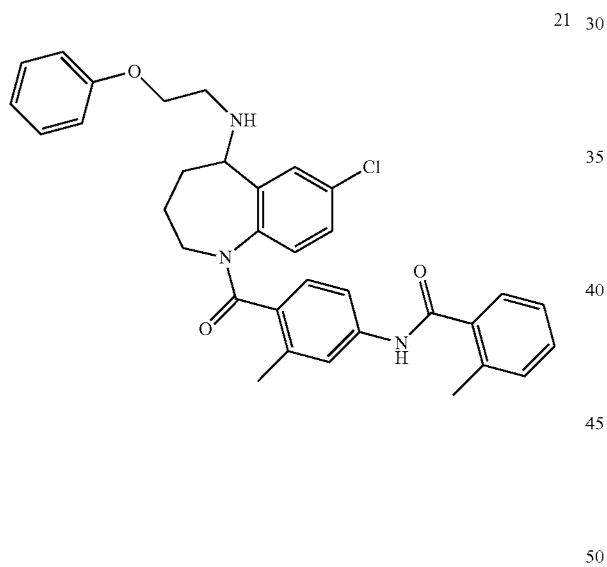

N-(3-aminopropyl)morpholine in step 2 of Example 1 was replaced with 2-phenoxyethylamine, and the rest of the required raw materials, reagents and preparation methods were the same as those in Step 2 of Example 1, Compound 21 was obtained as a white foam. $^1$H NMR (800 MHz, $CDCl_3$) δ 7.67-6.47 (m, 15H), 4.52-4.15 (m, 3H), 3.25-2.90 (m, 3H), 2.75-2.20 (m, 7H), 2.17-1.99 (m, 2H), 1.67-1.46 (m, 2H). HRMS (ESI) calculated for $C_{34}H_{35}ClN_3O_3^+$[M+H]$^+$568.2361; Found:568.2368.

Compounds 22-24 shown in Table 5 were prepared by using the corresponding intermediates essentially according to the method described in Example 9.

TABLE 5

| Compound No | Chemical name | Structural formula | Physical data (MS) $(M + H)^+$ |
|---|---|---|---|
| 22 | N-(4-(7-chloro-5-((3-phenoxypropyl)amino)-2,3,4,5-tetrahydro-1H-benzo[b]azepine-1-carbonyl)-3-methylphenyl)-2-methylbenzamide | 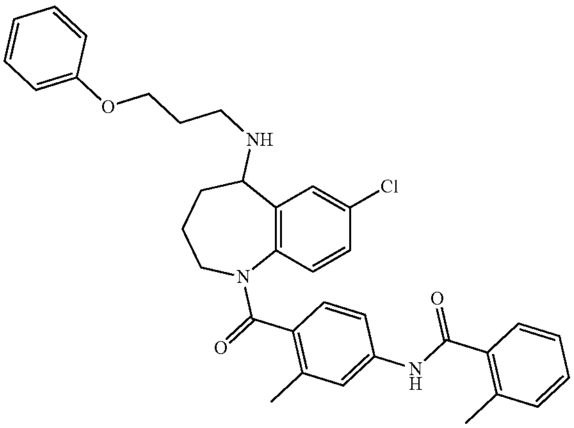 [SMILES: Cc1ccccc1C(=O)Nc1ccc(C(=O)N2CCCC(NCCCOc3ccccc3)c3cc(Cl)ccc32)c(C)c1] | 582.2518 |
| 23 | N-(4-(7-chloro-5-((4-phenoxybutyl)amino)-2,3,4,5-tetrahydro-1H-benzo[b]azepine-1-carbonyl)-3-methylphenyl)-2-methylbenzamide | 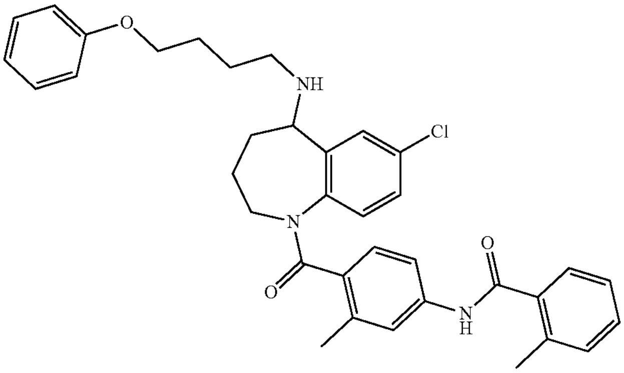 [SMILES: Cc1ccccc1C(=O)Nc1ccc(C(=O)N2CCCC(NCCCCOc3ccccc3)c3cc(Cl)ccc32)c(C)c1] | 596.2674 |
| 24 | N-(4-(7-chloro-5-((5-phenoxypentyl)amino)-2,3,4,5-tetrahydro-1H-benzo[b]azepine-1-carbonyl)-3-methylphenyl)-2-methylbenzamide | 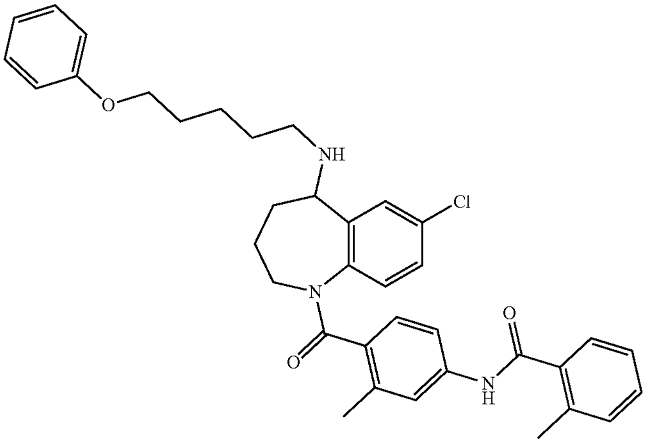 [SMILES: Cc1ccccc1C(=O)Nc1ccc(C(=O)N2CCCC(NCCCCCOc3ccccc3)c3cc(Cl)ccc32)c(C)c1] | 610.2831 |

Example 10

Preparation of N-(4-(7-chloro-5-((3-(diethylamino)propyl)amino)-2,3,4,5-tetrahydro-1H-benzo[b]azepine-1-carbonyl)-3-methylphenyl)-2-methylbenzamide (Compound 25):

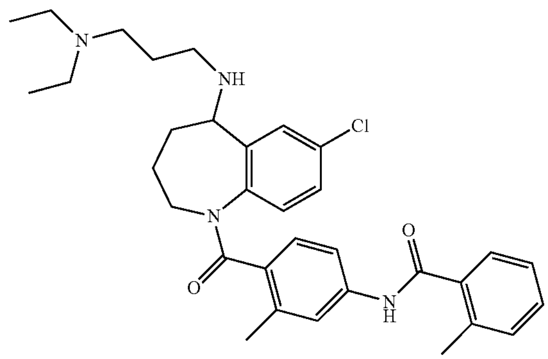

N-(3-aminopropyl)morpholine in step 2 of Example 1 was replaced with 3-diethylaminopropylamine, and the rest of the required raw materials, reagents and preparation methods were the same as those in step 2 of Example 1, Compound 25 was obtained as a white foam. $^1$H NMR (800 MHz, $CDCl_3$) δ 8.41-6.33 (m, 10H), 4.48-3.17 (m, 3H), 3.16-2.32 (m, 14H), 2.28-1.11 (m, 12H). HRMS (ESI) calculated for $C_{33}H_{42}ClN_4O_2^+$[M+H]$^+$561.2991; Found: 561.2990.

Compounds 26-28 shown in Table 6 were prepared by using the corresponding intermediates essentially according to the method in Example 10.

TABLE 6

| Compound No | Chemical name | Structural formula | Physical data (MS) (M + H)$^+$ |
|---|---|---|---|
| 26 | N-(4-(7-chloro-5-((2-(diethylamino)ethyl)amino)-2,3,4,5-tetrahydro-1H-benzo[b]azepine-1-carbonyl)-3-methylphenyl)-2-methylbenzamide | 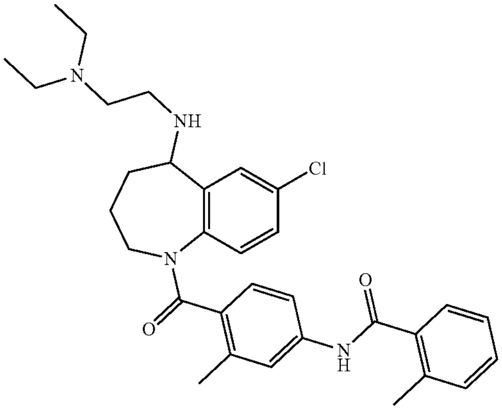 [SMILES: CCN(CC)CCNC1CCCN(C(=O)c2ccc(NC(=O)c3ccccc3C)cc2C)c2ccc(Cl)cc21] | 547.2834 |
| 27 | N-(4-(7-chloro-5-((4-(diethylamino)butyl)amino)-2,3,4,5-tetrahydro-1H-benzo[b]azepine-1-carbonyl)-3-methylphenyl)-2-methylbenzamide | 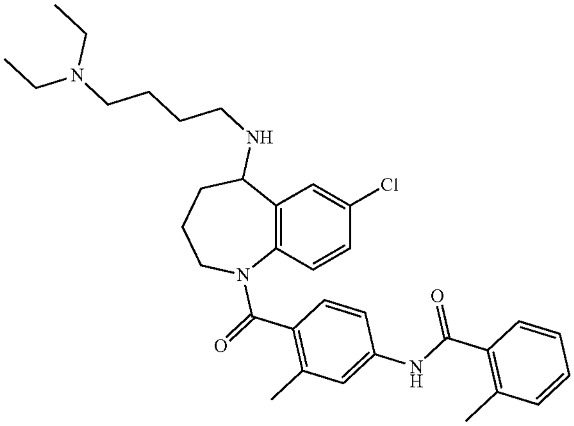 [SMILES: CCN(CC)CCCCNC1CCCN(C(=O)c2ccc(NC(=O)c3ccccc3C)cc2C)c2ccc(Cl)cc21] | 575.3147 |

TABLE 6-continued

| Compound No | Chemical name | Structural formula | Physical data (MS) $(M + H)^+$ |
|---|---|---|---|
| 28 | N-(4-(7-chloro-5-((5-(diethylamino)pentyl)amino)-2,3,4,5-tetrahydro-1H-benzo[b]azepine-1-carbonyl)-3-methylphenyl)-2-methylbenzamide | 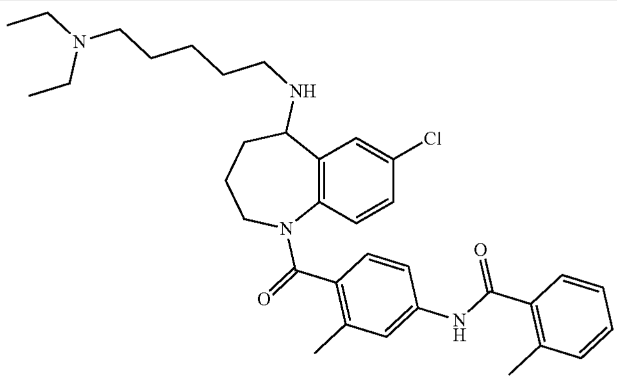 [SMILES: CCN(CC)CCCCCNC1CCCN(C(=O)c2ccc(NC(=O)c3ccccc3C)cc2C)c2ccc(Cl)cc21] | 589.3304 |

Example 11

Receptor Affinity Assay

In this experiment, fluorescence based methods were used, and the $k_{on}$ and $k_{off}$ of $V_2R$ fluorescent ligands were obtained by detecting the SB fluorescence intensity after binding of $V_2R$ fluorescent ligands with a final concentration of 6.3 nM to $V_2R$ expressed by cells at different time points. In this experiment, the $K_i$ and $IC_{50}$ of the tested compounds were obtained by detecting the SB fluorescence intensity after the binding of $V_2R$ fluorescent ligands with a final concentration of 6.3 nM to $V_2R$ expressed by cells at different concentrations of the compounds to be tested. Under the conditions of this experiment, the specific binding of $V_2R$ fluorescent ligands to $V_2R$ in the system could not be directly measured, and was obtained indirectly from the total binding minus non-specific binding: SB=TB−NSB.

The specific method was as follows. The TB signal at each concentration of the $V_2R$ fluorescent ligand was detected under the conditions of 620 nm and 665 nm by the multi-function microplate reader, after the association and dissociation between the $V_2R$ fluorescent ligand and the $V_2R$ expressed by the SNAP-tagged HEK293-h$V_2R$ cells reached an equilibrium state. The NSB signals at each concentration of $V_2R$ fluorescent ligand were the fluorescent signals generated by the non-specific binding of $V_2R$ fluorescent ligands in the system to the others except $V_2R$ in the system under the conditions of 620 nm and 665 nm, and were detected by a multifunctional microplate reader after the association and dissociation between the compound to be tested with a final concentration of 100 μM and $V_2R$ expressed by cells reached an equilibrium state, that is, after the compound fully antagonized the $V_2R$ in the system.

The specific operation steps were as follows. The compounds to be tested were diluted with Tag-lite assay buffer (1×) respectively to gradient concentrations with a final concentration of $1\times10^{-6}$-$1\times10^{-12}$ M. The above prepared compound, the solution of the compound to be tested with a final concentration of 100 μM, the Tag-lite assay buffer (1×) with a content of 1% DMSO, and the $V_2R$ fluorescent ligand with a final concentration of 6.3 nM were successively transferred to a 384-well plate to mix with the labeled SNAP-tagged HEK293-h$V_2R$ cells, incubating at 37° C. for 2 h. After the incubation, the experimental results were detected at 620 nm and 665 nm by the multifunctional microplate reader. After the detection, the ratio of SB fluorescence was calculated by the formula "fluorescence intensity at 665 nm/fluorescence intensity at 620 nm 10000". After the association and dissociation between $V_2R$ fluorescent ligand with a final concentration of 6.3 nM and the $V_2R$ expressed by cells reached an equilibrium and the compound to be tested in the system was at the lowest concentration, the ratio of the SB fluorescence intensities measured at 620 nm and 665 nm was taken as 100%. Then the ratios of the SB fluorescence measured after the association and dissociation between the $V_2R$ fluorescent ligand with a final concentration of 6.3 nM and the $V_2R$ reached an equilibrium and each compound to be tested was at different concentrations, were normalized.

The Association kinetics-One conc. of hot model in Graphpad Prism 7.0 was used to analyze the $k_{on}$ of $V_2R$ fluorescent ligands, and the Dissociation-One phase exponential decay model in Graphpad Prism 7.0 was used to analyze the $k_{off}$ of $V_2R$ fluorescent ligands. The One site-Fit $K_i$ and One site-Fit log $IC_{50}$ models in Graphpad Prism 7.0 were used to analyze the $K_i$ value and $IC_{50}$ value of the compound to be tested respectively. The results in Table 7 show that the affinity of each of Compounds 1, 4, 5, 9, and 13 to $V_2R$ is comparable to the affinity of Tolvaptan to $V_2R$. However, Compounds 1 and 4 exhibit longer residence time with receptor than Tolvaptan, and have better inhibitory effect than Tolvaptan on the development of vesicles in PKD disease, thus Compounds 1 and 4 have obvious advantages over Tolvaptan in delaying the progression of PKD.

TABLE 7

Receptor Affinity Array

| NO | $K_i$ (nM) | $k_{on}$ $(M^{-1}\cdot min^{-1})$ | $k_{off}$ $(min^{-1})$ | RT (min) |
|---|---|---|---|---|
| Tolvaptan | 1.7 ± 0.3 | $1.2 \pm 0.7 \times 10^8$ | 0.10 ± 0.01 | 10 ± 1 |
| Compound 1 | 11 ± 2 | $8.7 \pm 0.7 \times 10^6$ | 0.041 ± 0.005 | 25 ± 3 |
| Compound 2 | 31 ± 9 | $9.6 \pm 0.9 \times 10^6$ | 0.081 ± 0.011 | 12 ± 2 |
| Compound 3 | 39 ± 7 | $6.3 \pm 0.6 \times 10^6$ | 0.071 ± 0.009 | 14 ± 2 |
| Compound 4 | 6.9 ± 0.4 | $2.0 \pm 0.6 \times 10^7$ | 0.047 ± 0.004 | 21 ± 2 |
| Compound 5 | 10 ± 2 | $9.9 \pm 0.7 \times 10^6$ | 0.075 ± 0.007 | 13 ± 1 |
| Compound 9 | 13 ± 1 | $3.5 \pm 0.5 \times 10^7$ | 0.25 ± 0.04 | 4 ± 1 |

TABLE 7-continued

| Receptor Affinity Array | | | | |
|---|---|---|---|---|
| NO | $K_i$ (nM) | $k_{on}$ ($M^{-1} \cdot min^{-1}$) | $k_{off}$ ($min^{-1}$) | RT (min) |
| Compound 13 | 3.8 ± 0.4 | 4.1 ± 0.4 × $10^7$ | 0.11 ± 0.01 | 9 ± 1 |
| Compound 17 | 12 ± 2 | 2.1 ± 0.2 × $10^7$ | 0.14 ± 0.01 | 7 ± 1 |
| Compound 21 | 77 ± 26 | 1.1 ± 0.1 × $10^6$ | 0.060 ± 0.006 | 17 ± 2 |
| Compound 24 | 31 ± 7 | 1.1 ± 0.1 × $10^7$ | 0.15 ± 0.02 | 7 ± 1 |

Note:

The cell line used in this experiment is the human embryonic kidney 293 cell line (SNAP-tagged HEK293 $V_2R$ high expression cell, SNAP-tagged HEK293-$hV_2R$ cell) that highly expresses the human $V_2R$ protein carrying fluorophore;

$k_{on}$: association constant between the compound to be tested and cells;

$k_{off}$: dissociation constant between the compound to be tested and cells;

RT: residence time of the compound to be tested on cells.

Example 12

Vesicle Experiment

The vesicles similar to those in PKD disease are formed by using MDCK cells under the action of AC enzyme agonist forskolin to simulate the occurrence and development of the disease, and the test compounds are respectively administered to observe their effects on the vesicles.

Specific Operations:

1. Cell culture

The MDCK cells were cultured at 37° C./5% $CO_2$, with DMEM F12 medium (purchased from Combio technology company) supplemented with 10% fetal bovine serum and 1% double antibody. After cells were cultured for three days and had a growth area of about 80-90%, then the next step was started.

2. Preparation of matrigel (single well) according to the following formula

| | |
|---|---|
| Gel | 360 μL |
| 10% MEM | 40 μL |
| Hepes | 4 μL |
| NaOH | 6 μL (not fixed) |
| Cell | 2 μL (The concentration was about 40 × $10^4$ cells/mL, and about 600-800 cells were inoculated per well) |

3. Addition of digested cells to 24-well plate

During the re-cooling of matrigel, MDCK cells were digested and counted.

After the matrigel was prepared, the well plate was placed in the incubator to be stabilized for 90 minutes, and then 1.5 ml of cell culture medium containing 10 μM Forsklin and the drug with corresponding concentration was added to each well, the experiment was divided into: Control group, AMPK agonist (1 μM) group, AMPK agonist (3 μM) group, and AMPK agonist (10 μM) group. The cells were incubated for 12 days, in which the medium was changed every 12 h, and photos were taken at days 4, 6, 8, 10, and 12. The photo area was selected to track the specific vesicles.

The diameters of vesicles were compared on day 12 to assess the effect of test compounds. The experimental results are shown in Table 8.

TABLE 8

| PKD vesicle experiment | |
|---|---|
| Compound | The diameter of vesicles (μm) |
| Control | 217.6 |
| Compound 1 | 172.0 |
| Tolvaptan | 183.7 |

The results of the vesicle experiment show that, compared with the control group, such compounds could significantly inhibit the development of vesicles in PKD diseases, and the compounds have better inhibitory effect than Tolvaptan on the development of vesicles in PKD diseases.

Example 13

PKD Mouse Experiment

Such compounds have antagonistic effects on arginine vasopressin receptors, and can inhibit the effect of cAMP in vivo, thereby inhibiting the occurrence and development of PKD. In this experiment, PKD1 knockout mice were used to evaluate the efficacy of these compounds.

Specific Operations:

1. Numbering the mice to perform gene identification: After 3 days of birth, the mice were marked by the method of cutting toes. The cut toes were placed in EP tubes marked in advance to boil, and then the genes were identified by agarose electrophoresis after PCR.
2. Preparation of corresponding medicaments: The corresponding weights of drugs were precisely weighed with an electronic balance and placed in new EP tubes. Then the corresponding amounts of HPMC were added with a pipette to prepare the medicaments of the desired concentration. (Taking 2 mg/kg of Compound 1 as an example, 1 mg of Compound 1 was weighed and 500 μL of HPMC was added to vortex for 30 s (to suspend most of the drug), then sonicating for 15-20 minutes to crush large pieces of drug, and then vortexing for 30 s.
3. Administration to mice: The administrations of medicaments to mice was started on Day 6 or 5 after birth (the underweight mice were administered with medicaments on Day 6, and the rest of mice were administered with medicaments on Day 5), and the administration time was fixed (for example, 9:00 am). The target mouse (back) was pinched with the index finger and thumb, after weighing the mouse, corresponding amount of the medicament was sucked with a microinjector, and the microinjector was insert into the bump on the back of the mouse (between the thumb and index finger) to perform subcutaneous injection.
4. Extraction of mice tissue: The mice were killed after seven days of administration, and were precisely weighed. The laparotomy was performed to harvest and precisely weigh the left kidney. The kidney was placed in the middle of the horizontal line to photograph it, then placing in a numbered EP tube to temporarily store on ice. The right kidney was then harvested to weigh and photograph under the same conditions, then placing in a numbered EP tube to preserve in paraformaldehyde. The liver was harvested to place in a numbered EP tube to temporarily store on ice. After the operations were completed, the liver and left kidney were stored in a refrigerator at −80 degree Celsius.

5. Data processing: The total weight of the left and right kidneys, and the proportion of the kidneys, etc. were calculated. The experimental results are shown in Table 9.

TABLE 9

| PKD mouse experiment | | |
|---|---|---|
| Compound | Dosage (mg/kg) | Proportion of the kidneys % |
| Control | | 21.97 |
| Compound 1 | 2 | 11.85 |
| Tolvaptan | 2 | 15.80 |

The results of animal experiments show that, compared with the control group, such compounds can obviously delay the occurrence and development of PKD, that is, such compounds have a therapeutic effect on PKD and are better than that of Tolvaptan.

The above experiments show that such compounds can effectively inhibit the occurrence and development of vesicles and slow down the progression of PKD disease by antagonizing the arginine vasopressin receptor. Therefore, such compounds have potential application in the treatment of PKD.

Example 14

In order to more fully illustrate the pharmaceutical composition of the present application, a formulation example is provided below, and this example is only used for illustration and not to limit the scope of the present application. The formulation may be used for any active compound of present application and a salt thereof, and is illustrated by the compound described in Example 1. Hard gelatin capsules were prepared according to the ingredients and amounts in Table 10:

TABLE 10

| | Doage/capsule |
|---|---|
| Compound 1 | 20 mg |
| Starch | 300 mg |
| Magnesium stearate | 25 mg |

Preparation process: The raw materials were pre-dried and passed through a 100-mesh sieve for use. The above ingredients were mixed well according to the prescribed amounts to fill into hard gelatin capsules.

Although multiple examples are described in the present application, it should be understood that various changes and modifications will be apparent to those skilled in the art without departing from the spirit and scope of the application. Such changes and modifications are intended to be included within the scope of the appended claims of the present application.

The invention claimed is:

1. A compound of formula (I) or a stereoisomer thereof or a pharmaceutically acceptable salt thereof, (I)

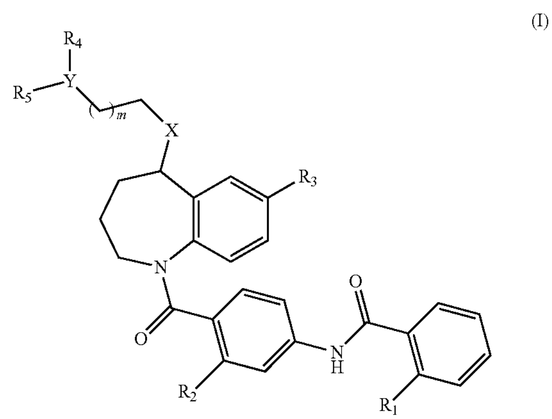

wherein

X is NH;

Y is selected from N, CH or S;

$R_1$, $R_2$ and $R_3$ are each independently selected from hydrogen, halogen, cyano, nitro, hydroxy, amino, $C_{1-6}$ alkyl, $C_{1-6}$ alkoxy, or $C_{3-8}$ cycloalkyl;

$R_4$ is selected from hydrogen, halogen, cyano, nitro, hydroxy, amino, $C_{1-6}$ alkyl, $C_{1-6}$ alkoxy, $C_{3-8}$ cycloalkyl, aryl, heteroaryl, heterocyclyl, heterocyclyl-$(CH_2)$n-, aryl-$C_{1-6}$ alkyl-, heteroaryl-$C_{1-6}$ alkyl-, aryl-$(CH_2)$n-O—, heteroaryl-$(CH_2)$n-O—, $C_{3-8}$ cycloalkyl-C(O)—, heterocyclyl-C(O)—, aryl-C(O)—, or heteroaryl-C(O), wherein each of $C_{1-6}$ alkyl,$C_{1-6}$ alkoxy, $C_{3-8}$ cycloalkyl, aryl, heteroaryl, heterocyclyl, heterocyclyl-$(CH_2)$n-, aryl-$C_{1-6}$ alkyl-,heteroaryl-$C_{1-6}$ alkyl-, aryl-$(CH_2)$n-O—, heteroaryl-$(CH_2)$n-O—, $C_{3-8}$ cycloalkyl-C(O)—, heterocyclyl-C(O)—, aryl-C(O)—, or heteroaryl-C(O) is unsubstituted or substituted with at least one substituent selected from halogen, $C_{1-6}$ alkyl, $C_{1-6}$ cycloalkyl, or heterocyclyl;

$R_5$ is selected from

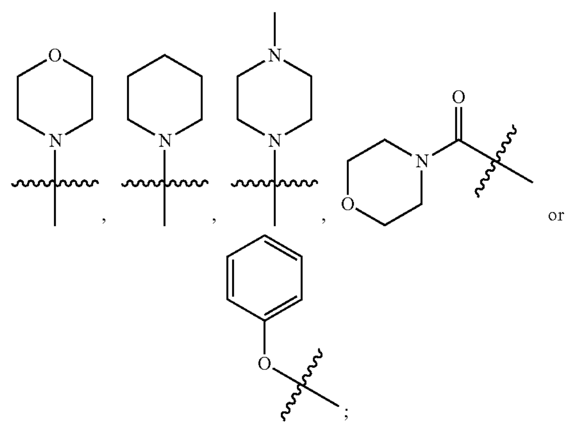

, , , or ;

m is 0, 1, 2, 3 or 4;

n is 0, 1, 2, 3 or 4.

2. The compound or a stereoisomer thereof or a pharmaceutically acceptable salt thereof according to claim 1, wherein Y is selected from N or CH.

3. The compound or a stereoisomer thereof or a pharmaceutically a cceptable salt thereof according to claim 1, wherein $R_4$ is hydrogen or $C_{1-6}$ alkyl.

4. The compound or a stereoisomer thereof or a pharmaceutically acceptable salt thereof according to claim 3, wherein $R_4$ is hydrogen.

5. The compound or a stereoisomer thereof or a pharmaceutically acceptable salt thereof according to claim 1, wherein $R_4$ is $C_{1-6}$ alkyl.

6. A compound of stereoisomer thereof or a pharmaceutically acceptable salt thereof, wherein the compound is selected from the group consisting of:

1) N-(4-(7-chloro-5-((3-morpholinopropyl)amino)-2,3,4,5-tetrahydro-1H-benzo[b]azepine-1-carbonyl)-3-methylphenyl)-2-methylbenzamide;
2) N-(4-(7-chloro-5-((4-morpholinobutyl)amino)-2,3,4,5-tetrahydro-1H-benzo[b]azepine-1-carbonyl)-3-methylphenyl)-2-methylbenzamide;
3) N-(4-(7-chloro-5-((5-morpholinopentyl)amino)-2,3,4,5-tetrahydro-1H-benzo[b]azepine-1-carbonyl)-3-methylphenyl)-2-methylbenzamide;
4) N-(4-(7-chloro-5-((2-morpholinoethyl)amino)-2,3,4,5-tetrahydro-1H-benzo[b]azepine-1-carbonyl)-3-methylphenyl)-2-methylbenzamide;
5) N-(4-(7-chloro-5-((3-(pyridin-4-yl)propyl)amino)-2,3,4,5-tetrahydro-1H-benzo[b]azepine-1-carbonyl)-3-methylphenyl)-2-methylbenzamide;
6) N-(4-(7-chloro-5-((2-(pyridin-4-yl)ethyl)amino)-2,3,4,5-tetrahydro-1H-benzo[b]azepine-1-carbonyl)-3-methylphenyl)-2-methylbenzamide;
7) N-(4-(7-chloro-5-((4-(pyridin-4-yl)butyl)amino)-2,3,4,5-tetrahydro-1H-benzo[b]azepine-1-carbonyl)-3-methylphenyl)-2-methylbenzamide;
8) N-(4-(7-chloro-5-((5-(pyridin-4-yl)pentyl)amino)-2,3,4,5-tetrahydro-1H-benzo[b]azepine-1-carbonyl)-3-methylphenyl)-2-methylbenzamide;
9) N-(4-(7-chloro-5-((3-(piperidin-1-yl)propyl)amino)-2,3,4,5-tetrahydro-1H-benzo[b]azepine-1-carbonyl)-3-methylphenyl)-2-methylbenzamide;
10) N-(4-(7-chloro-5-((2-(piperidin-1-yl)ethyl)amino)-2,3,4,5-tetrahydro-1H-benzo[b]azepine-1-carbonyl)-3-methylphenyl)-2-methylbenzamide;
11) N-(4-(7-chloro-5-((4-(piperidin-1-yl)butyl)amino)-2,3,4,5-tetrahydro-1H-benzo[b]azepine-1-carbonyl)-3-methylphenyl)-2-methylbenzamide;
12) N-(4-(7-chloro-5-((5-(piperidin-1-yl)pentyl)amino)-2,3,4,5-tetrahydro-1H-benzo[b]azepine-1-carbonyl)-3-methylphenyl)-2-methylbenzamide;
13) N-(4-(7-chloro-5-((3-morpholino-3-oxopropyl)amino)-2,3,4,5-tetrahydro-1H-benzo[b]azepine-1-carbonyl)-3-methylphenyl)-2-methylbenzamide;
14) N-(4-(7-chloro-5-((4-morpholino-4-oxobutyl)amino)-2,3,4,5-tetrahydro-1H-benzo[b]azepine-1-carbonyl)-3-methylphenyl)-2-methylbenzamide;
15) N-(4-(7-chloro-5-((5-morpholino-5-oxopentyl)amino)-2,3,4,5-tetrahydro-1H-benzo[b]azepine-1-carbonyl)-3-methylphenyl)-2-methylbenzamide;
16) N-(4-(7-chloro-5-((6-morpholino-6-oxohexyl)amino)-2,3,4,5-tetrahydro-1H-benzo[b]azepine-1-carbonyl)-3-methylphenyl)-2-methylbenzamide;
17) N-(4-(7-chloro-5-((3-(4-methylpiperazin-1-yl)propyl)amino)-2,3,4,5-tetrahydro-1H-benzo[b]azepine-1-carbonyl)-3-methylphenyl)-2-methylbenzamide;
18) N-(4-(7-chloro-5-((2-(4-methylpiperazin-1-yl)ethyl)amino)-2,3,4,5-tetrahydro-1H-benzo[b]azepine-1-carbonyl)-3-methylphenyl)-2-methylbenzamide;
19) N-(4-(7-chloro-5-((4-(4-methylpiperazin-1-yl)butyl)amino)-2,3,4,5-tetrahydro-1H-benzo[b]azepine-1-carbonyl)-3-methylphenyl)-2-methylbenzamide;
20) N-(4-(7-chloro-5-((5-(4-methylpiperazin-1-yl)pentyl)amino)-2,3,4,5-tetrahydro-1H-benzo[b]azepine-1-carbonyl)-3-methylphenyl)-2-methylbenzamide;
21) N-(4-(7-chloro-5-((2-phenoxyethyl)amino)-2,3,4,5-tetrahydro-1H-benzo[b]azepine-1-carbonyl)-3-methylphenyl)-2-methylbenzamide;
22) N-(4-(7-chloro-5-((3-phenoxypropyl)amino)-2,3,4,5-tetrahydro-1H-benzo[b]azepine-1-carbonyl)-3-methylphenyl)-2-methylbenzamide;
23) N-(4-(7-chloro-5-((4-phenoxybutyl)amino)-2,3,4,5-tetrahydro-1H-benzo[b]azepine-1-carbonyl)-3-methylphenyl)-2-methylbenzamide;
24) N-(4-(7-chloro-5-((5-phenoxypentyl)amino)-2,3,4,5-tetrahydro-1H-benzo[b]azepine-1-carbonyl)-3-methylphenyl)-2-methylbenzamide;
25) N-(4-(7-chloro-5-((3-(diethylamino)propyl)amino)-2,3,4,5-tetrahydro-1H-benzo[b]azepine-1-carbonyl)-3-methylphenyl)-2-methylbenzamide;
26) N-(4-(7-chloro-5-((2-(diethylamino)ethyl)amino)-2,3,4,5-tetrahydro-1H-benzo[b]azepine-1-carbonyl)-3-methylphenyl)-2-methylbenzamide;
27) N-(4-(7-chloro-5-((4-(diethylamino)butyl)amino)-2,3,4,5-tetrahydro-1H-benzo[b]azepine-1-carbonyl)-3-methylphenyl)-2-methylbenzamide; and
28) N-(4-(7-chloro-5-((5-(diethylamino)pentyl)amino)-2,3,4,5-tetrahydro-1H-benzo[b]azepine-1-carbonyl)-3-methylphenyl)-2-methylbenzamide.

7. The compound or a stereoisomer thereof or a pharmaceutically acceptable salt thereof according to claim 1, wherein the pharmaceutically acceptable salt is a salt formed by reacting the compound with an inorganic acid or an organic acid.

8. A pharmaceutical composition, comprising a therapeutically effective amount of the compound, or a stereoisomer thereof or a pharmaceutically acceptable salt thereof according to claim 1, and one or more pharmaceutically acceptable carrier.

9. A method for treating polycystic kidney disease, comprising administering to a subject the compound or a stereoisomer thereof or a pharmaceutically acceptable salt thereof according to claim 1.

10. The method according to claim 9, wherein the subject is a mammal.

11. The method according to claim 10, wherein the mammal includes a human, a non-human primate, a rabbit, a sheep, a rat, a dog, a cat, a pig, or a mouse.

12. The compound or a stereoisomer thereof or a pharmaceutically acceptable salt thereof according to claim 1, wherein $R_1$ and $R_2$ are each independently selected from $C_{1-6}$ alkyl, and $R_3$ is halogen.

13. The compound or a stereoisomer thereof or a pharmaceutically acceptable salt thereof according to claim 1, wherein both $R_1$ and $R_2$ are methyl, and $R_3$ is chlorine.

14. The compound or a stereoisomer thereof or a pharmaceutically acceptable salt thereof according to claim 7, wherein the inorganic acid is hydrochloric acid, hydrobromic acid, sulfuric acid or phosphoric acid, and the organic acid is citric acid, lactic acid, malic acid, gluconic acid, tartaric acid, adipic acid, acetic acid, succinic acid, fumaric acid, ascorbic acid, itaconic acid, methanesulfonic acid or benzenesulfonic acid.

* * * * *